(12) United States Patent
Nishi et al.

(10) Patent No.: US 7,195,892 B2
(45) Date of Patent: Mar. 27, 2007

(54) ACYLASE GENE

(75) Inventors: Akiko Nishi, Akashi (JP); Takumi Mano, Tatsuno (JP); Shinichi Yokota, Kakogawa (JP); Masayuki Takano, Kakogawa (JP); Kazuyoshi Yajima, Akashi (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/516,587

(22) PCT Filed: May 30, 2003

(86) PCT No.: PCT/JP03/06807

§ 371 (c)(1),
(2), (4) Date: Jun. 24, 2005

(87) PCT Pub. No.: WO03/104446

PCT Pub. Date: Dec. 18, 2003

(65) Prior Publication Data

US 2006/0035363 A1    Feb. 16, 2006

(30) Foreign Application Priority Data

Jun. 6, 2002 (JP) .............................. 2002-165722

(51) Int. Cl.
*C12P 35/00* (2006.01)
*C12P 21/00* (2006.01)
*C12N 9/84* (2006.01)
*C12N 1/20* (2006.01)
*C07H 21/04* (2006.01)

(52) U.S. Cl. ............... 435/47; 435/230; 435/320.1; 435/252.33; 435/69.1; 435/252.3; 536/23.2; 536/23.1; 536/23.7; 536/24.1

(58) Field of Classification Search ............ 435/47, 435/69.1, 230, 252.33, 320.1
See application file for complete search history.

(56) References Cited

U.S. PATENT DOCUMENTS 5,168,048 A    12/1992    Quax

FOREIGN PATENT DOCUMENTS

JP    4-228073    12/1992

OTHER PUBLICATIONS

Crowder, Michael, W., et al., Overexpression, Purification, and Characterization of the Cloned Metallo-β-Lactamase L1 from *Stenotrophomonas maltophilia*, Antimicrobial Agents and Chemotherapy, vol. 42, No. 4, Apr. 1998, p. 921-926.
Hernández-Jústiz, O., et al., Evaluation of different enzymes as catalysts for the production of β-lactam antibiotics following a kinetically controlled strategy, Enzyme and Microbial Technology Apr. 25, 1999, p. 336-343.
Simpson et al., "The genome sequence of the plant pathogen *Xylella fastidiosa*," Nature, vol. 408, pp. 151-157 (Jul. 13, 2000).
Kim et al., "Characterization of Glutaryl 7-ACA Acylase from *Pseudomonas diminuta* KAC-1," J. Microbiology and Biotechnology (The Korean Society for Applied Microbiology), vol. 11, No. 3, pp. 452-457 (2001, Seoul, S. Korea).
Elander, "Industrial production of β-lactam antibiotics," Applied Microbiology and Biotechnology, vol. 61, pp. 385-392 (2003).
Sio et al., "Improved β-lactam acylases and their use as industrial biocatalysts," Current Opinion in Biotechnology, vol. 15, pp. 349-355 (2004).
Database UniProt (Online), Oct. 1, 2000, "Glutaryl-7-ACA Acylase", Amino Acid Sequence, Accession No. Q9PEJ9, XP-002375572.

*Primary Examiner*—Rebecca E. Prouty
*Assistant Examiner*—Malgorzata A. Walicka
(74) *Attorney, Agent, or Firm*—Kenyon & Kenyon LLP

(57) ABSTRACT

The subject of the present invention is to provide a β-lactam acylase protein having high activity, a gene coding for said β-lactam acylase protein, a recombinant vector having said gene, a transformant containing said recombinant vector, and a method of producing a β-lactam antibiotic such as amoxycillin using said β-lactam acylase. A β-lactam acylase gene of *Stenotrophomonas maltophilia* was cloned, the DNA base sequence and the amino acid sequence expected therefrom was determined, and a *Stenotrophomonas* β-lactam acylase gene was obtained. This gene was found to code for a protein with a molecular weight of about 70 kDa and having β-lactam acylase activity, and could efficiently produce amoxycillin without being inhibited by phenylacetic acid, etc. Furthermore, by modification of the amino acid sequence, a protein which can more efficiently produce amoxycillin could be obtained.

24 Claims, 4 Drawing Sheets

ACYLASE GENE

This application is a 371 national phase application of PCT/JP03/06807 filed on 30 May 2003, claiming priority to JP 2002-165722, filed on 06 Jun. 2002, the contents of which are incorporated herein by reference in their entireties.

TECHNICAL FIELD

The present invention relates to a gene having a DNA coding for a β-lactam acylase of *Stenotrophomonas*, a modified gene thereof having reduced substrate decomposition activity and enhanced acylase activity, a protein expected from the base sequence of said gene, a β-lactam acylase coded by said gene, a recombinant vector having said gene, a transformant containing said recombinant vector, a method of producing said enzyme, and a method of producing a β-lactam antibiotic using said enzyme.

BACKGROUND ART

Many of β-lactam antibiotics including amoxycillin, ampicillin and cephalosporin are produced by using, as a starting material, a fermentation product obtained by culturing bacteria such as those belonging to the genera *Penicillium* and *Cephalosporium*.

For example, for producing 6-aminopenicillanic acid (6-APA) or 7-aminocephalosporanic acid (7-ACA), which is the most important intermediate for the industrial production of a semisynthetic penicillin and cephalosporin, by cleaving an amide bond (deacylation) of penicillin G (PenG), penicillin V (PenV) or cephalosporin C, penicillin G acylase (benzyl penicillin amide hydrolase, also called penicillin G amidase, EC 3.5.1.11) has commercially been used. This enzyme is also used industrially for converting phenylacetyl-7-aminodeacetoxycephalosporanic acid, which is chemically produced from PenG generally, into 7-aminodeacetoxycephalosporanic acid (7-ADCA). Semisynthetic penicillins and cephalosporins produced by chemical synthesis reactions between these β-lactam cores 6-APA, 7-ACA and 7-ADCA with side chain compounds form an important market of β-lactam antibiotics.

Enzymes which have been conventionally useful in deacylation for producing the β-lactam core are classified as hydrolysis enzymes, and usually called "acylase" or "amidase" in said field. Among these acylase enzymes, ones recognizing a β-lactam antibiotic as a substrate are further specified as "β-lactam acylases". In the β-lactam acylase activities, there are hydrolysis (deacylation) activity in the case where an acyl group is detached by water, and transfer activity catalyzing transfer of an acyl group from an activated side chain substrate into a nucleophilic substance as a reverse reaction. This chemical form is represented by the following general formula. That is, in the compound acceptable as a substrate by a specific acylase: X—CO—NH—Y, the characteristics of said chemical forms X and Y are defined according to the substrate specificity of the correspond acylase. X represents a side chain, and Y represents an acyl acceptor group. For example, in the case of PenG, X—CO— represents a phenylacetyl side chain, and —NH—Y represents 6-APA. These β-lactam acylases attract attention for having possibility to convert an acyl group transfer reaction process from a chemical synthesis method to an enzyme method in producing β-lactam antibiotics, but they have not been put into practical use yet due to their poor production efficiencies.

β-lactam acylases are classified as follows according to the substrate specificity and molecular characteristics (Process Biochemistry, 27, 131, 1992, World J. Microbiology & Biotechnology, 10, 129, 1994). β-lactam acylases are broadly classified into penicillin acylases and cephalosporin acylases. Penicillin acylases are further classified into penicillin G acylases, penicillin V acylases and ampicillin acylases. Cephalosporin acylases are further classified into cephalosporin acylases and glutaryl-7-ACA (GL-7-ACA) acylases.

Penicillin G acylases, which have been commercially used for producing 6-APA, etc., form heterodimers consisting of a small subunit (α: 16 to 26 kDa) and a large subunit (α: 54 to 66 kDa). On the other hand, penicillin V acylases are known to form tetramers of a subunit having a molecular weight of 35 KDa, and ampicillin acylases are known to form homodimers having a molecular weight of 72 kDa. Moreover, from their substrate specificities, some of them have the name of α-amino acid hydrolases, but these cases are also included in the above acylase activity for the chemical reaction form.

Among these acylases, acylase gene sequences of the microorganisms coding for penicillin G acylase have been clarified. That is, there are *Escherichia coli* (Nucleic Acids Res., 14 (14), 5713, 1996), *Kluyvera citrophila* (Gene, 49, 69, 1986), *Alcaligenes faecalis* (Japanese Kokai Publication Hei-4-228073), *Providencia rettgeri* (DNA seq., 3, 195, 1992), *Arthrobacter viscosus* (Appl. Environ. Microbiol., 54, 2603, 1988), *Archaeoglobus fulgidus* (Nature, 390, 364, 1997), *Bacillus megaterium* (FEMS Microbiol. Lett. 125, 287, 1995), and the like. Moreover, as for GL-7-ACA acylase having a heterodimer structure, *Pseudomonas* sp. (J. Ferment. Bioeng., 77, 591, 1994) is clarified, and as for cephalosporin acylase, *Pseudomonas* sp. (J. Bacteriol., 163, 1222, 1985, J. Bacteriol., 169, 5821, 1987), etc. have been clarified.

Since these are clarified at the DNA levels as gene families, gene clonings are easy, and the DNA acquisition by carrying out screening by a method using an enzymatic activity of a microorganism genome library as the index is also easily possible.

SUMMARY OF THE INVENITON

The subject which the present invention is to solve is to provide a β-lactam acylase protein with high activity, a gene coding for said β-lactam acylase protein, a recombinant vector having said gene, a transformant containing said recombinant vector, and a method of producing a β-lactam antibiotic such as amoxycillin using said β-lactam acylase. Since the conventional penicillin G acylase is low in synthetic efficiency into a β-lactam antibiotic such as amoxycillin, and the synthesis activity is strongly inhibited by phenylacetic acid, phenoxyacetic acid, or amoxycillin, the development of an enzyme improved with these properties has been demanded for that would be industrially great advantage.

The present inventors carried out screening of various strains from soil aiming at obtaining an enzyme efficiently producing amoxycillin from 6-aminopenicillanic acid (6-APA) and D-p-hydroxyphenylglycine methyl ester (HPGOMe). As a result, they found that microorganisms belonging to the genus *Stenotrophomonas*, which are gram negative bacteria, produce a β-lactam acylase. From this bacteria, a β-lactam acylase was purified and the gene cloning was carried out. As a result, a DNA base sequence shown under SEQ ID NO:1 was determined by cloning the β-lactam acylase gene. The "gene" referred to in the present invention is a nucleotide sequence having functions, and for example, a region on a nucleic acid defining the primary structures of protein, tRNA, rRNA, etc. or a region on a nucleic acid having control functions such as a transcription regulatory region for mRNA and a translation regulatory region for protein are included. It was revealed that the open reading frame of said gene comprises 1911 bases, and codes for a protein having a molecular weight of about 70 kDa and comprising 636 amino acid sequences shown under SEQ ID NO:2. Moreover, said gene was expressed in a host, and confirmed to have acylation activity. Furthermore, in said structural gene, by substituting the 735th adenine in the DNA base sequence shown under SEQ ID NO:1 with guanine, and mutating the 204th methionine in the amino acid sequence shown under SEQ ID NO:2 to valine, the inventors have succeeded in producing a modified acylase having reduced ester decomposition activity of the substrate D-p-hydroxyphenylglycine methyl ester (HPGOMe) and enhanced acylase activity, thereby completed the present invention.

The β-lactam acylase-producing bacteria of the invention belong to the genus *Stenotrophomonas*, and the *Stenotrophomonas maltophilia* KNK12A strain which the present inventors isolated from soil is one example of strains which can be most efficiently used in the present invention.

That is, the present invention relates to a β-lactam acylase produced by a microorganism belonging to the genus *Stenotrophomonas*, a β-lactam acylase produced by the *Stenotrophomonas maltophilia* KNK12A strain, and a modified acylase having enhanced acylase activity by reducing ester decomposition activity of the substrate D-p-hydroxyphenylglycine methyl ester (HPGOMe) of said enzyme.

In addition, the present invention relates to a gene which contains a DNA coding for a protein comprising an amino acid sequence identical or substantially identical with the amino acid sequence shown under SEQ ID NO:2, a gene which contains a DNA coding for a protein in which the 204th methionine in the amino acid sequence shown under SEQ ID NO:2 is substituted with valine, a gene which contains a DNA coding for a protein in which the 204th methionine in the amino acid sequence shown under SEQ ID NO:2 is substituted, a gene which contains a DNA coding for a protein comprising an amino acid sequence in which one or a plurality of amino acids in the amino acid sequence shown under SEQ ID NO:2 have undergone deletion, substitution or addition and having β-lactam acylase activity, and a gene which contains a DNA coding for a protein in which the amino acid sequence shown under SEQ ID NO:2 is modified after translation and having β-lactam acylase activity.

Furthermore, the present invention relates to a gene which contains a DNA in which the base sequence corresponding to the site coding for the amino acid sequence shown under SEQ ID NO:2 in the base sequence shown under SEQ ID NO:1 codes for the amino acid sequence identical with the amino acid sequence shown under SEQ ID NO:2. Furthermore, the invention relates to the above gene which is isolated from microorganisms belonging to the genus *Stenotrophomonas*.

Furthermore, the invention relates to a microorganism which produces a protein comprising an amino acid sequence identical or substantially identical with the amino acid sequence shown under SEQ ID NO:2 and belongs to the genus *Stenotrophomonas*.

Furthermore, the invention relates to a polynucleotide which contains a base sequence coding for a protein comprising an amino acid sequence identical or substantially identical with the amino acid sequence shown under SEQ ID NO:2, a polynucleotide which contains a base sequence coding for a protein in which the 204th methionine in the amino acid sequence shown under SEQ ID NO:2 is substituted with valine, a polynucleotide which contains a base sequence coding for a protein in which the 204th methionine in the amino acid sequence shown under SEQ ID NO:2 is substituted, a polynucleotide which contains a base sequence coding for a protein comprising an amino acid sequence in which one or a plurality of amino acids in the amino acid sequence shown under SEQ ID NO:2 have undergone deletion, substitution or addition and having β-lactam acylase activity, a polynucleotide which contains a base sequence coding for a protein in which the amino acid sequence shown under SEQ ID NO:2 is modified after translation and having β-lactam acylase activity, a polynucleotide which contains a base sequence in which the base sequence corresponding to the site coding for the amino acid sequence shown under SEQ ID NO:2 in the base sequence shown under SEQ ID NO:1 codes for the amino acid sequence identical with the amino acid sequence shown under SEQ ID NO:2, a polynucleotide which contains the base sequence shown under SEQ ID NO:1, and the above polynucleotide which is isolated from a microorganism belonging to the genus *Stenotrophomonas*.

Furthermore, the invention relates to a protein which comprises an amino acid sequence identical or substantially identical with the amino acid sequence shown under SEQ ID NO:2, a protein which comprises an amino acid sequence in which the 204th methionine in the amino acid sequence shown under SEQ ID NO:2 is substituted with valine, a protein which comprises an amino acid sequence in which the 204th methionine in the amino acid sequence shown under SEQ ID NO:2 is substituted, and a protein which comprises an amino acid sequence in which one or a plurality of amino acids in the amino acid sequence shown under SEQ ID NO:2 have undergone deletion, substitution or addition and having β-lactam acylase activity.

Furthermore, the invention relates to a protein in which the amino acid sequence shown under SEQ ID NO:2 is modified after translation and having β-lactam acylase activity.

Furthermore, the invention relates to a gene which contains a transcription regulatory sequence contained in the above gene, a gene which contains a translation regulatory sequence contained in the above gene, and the above gene under the control of regulon containing a transcription and/or translation regulatory sequence, wherein either or both of said regulatory sequence(s) is (are) substituted with other transcription and/or translation regulatory sequence each obtainable by the same or different living organism.

Furthermore, the invention relates to a recombinant vector which comprises at least one of the above gene, a transformant which is obtainable by transforming a host with the above recombinant vector, the above transformant wherein the host is a gram-negative microorganism, the above transformant wherein the host is a gram-positive microorganism, the above transformant which is pUCNTkmTn5-KNK-L/HB101 (FERM BP-8362), and the above transformant which is pUCNT-Tn5-MuKNK-L1/HB101 (FERM BP-8369).

Furthermore, the invention relates to a method of producing a β-lactam acylase which comprises culturing the above transformant, and recovering a β-lactam acylase produced by said transformant, a β-lactam acylase which comprises an amino acid sequence coded by the above polynucleotide, and an immobilized β-lactam acylase which is obtainable by culturing the above microorganism or the above transformant, and immobilizing the cell, cell-mixed culture, cell disrupted product, or a β-lactam acylase extracted and/or purified from the cell.

Furthermore, the invention relates to a method of producing a β-lactam acylase in a transformant or of enhancing the production which comprises preparing the above recombinant vector, transforming a host with said recombinant vector, cloning the obtained transformant, and selecting.

Furthermore, the invention relates to a method of producing a β-lactam antibiotic such as amoxycillin using said enzyme.

Furthermore, the invention relates to a method of producing a β-lactam antibiotic such as amoxycillin using a β-lactam acylase comprising an amino acid sequence coded by the above polynucleotide.

The β-lactam acylase enzyme of *Stenotrophomonas* according to the present invention does not show the characteristic homology with the reported gene sequences of the *Escherichia coli* penicillin G acylase (Nucleic Acids Res., 14(14), 5713, 1996), *Kluyvera citrophila* penicillin G acylase (Gene, 49, 69, 1986), *Alcaligenes faecalis* penicillin G acylase (Japanese Kokai Publication Hei-4-228073), *Providencia rettgeri* penicillin G acylase (DNA seq., 3, 195, 1992), *Arthrobacter viscosus* penicillin G acylase (Appl. Environ. Microbiol., 54, 2603, 1988), *Archaeoglobus fulgidus* penicillin acylase (Nature, 390, 364, 1997), *Bacillus megaterium* penicillin G acylase (FEMS Microbiol. Lett., 125, 287, 1995), *Pseudomonas* C427 GL-7ACA acylase (J. Ferment. Bioeng., 77, 591, 1994), *Pseudomonas* GK 16 cephalosporin acylase (J. Bacteriol., 163, 1222, 1985), and *Pseudomonas* SE83 cephalosporin acylase (J. Bacteriol., 169, 5821, 1987). In addition, there is no report on the DNA sequence and amino acid sequence regarding the β-lactam acylase of *Stenotrophomonas*.

In the process for acquiring an enzyme gene, the present inventors also attempted a usual acylase enzymatic activity measurement screening from the *Stenotrophomonas maltophilia* KNK12A strain genome library, but a positive clone showing activity could not be obtained. It was presumed that this is because the promoter of the β-lactam acylase itself does not have or has only low RNA transcription activity in the host *Escherichia coli*, an enzyme is not expressed, or the expression is very weak.

DETAILED DESCRIPTION OF THE INVENTION

Hereinafter, the present invention is described in detail.

The gene referred to herein represents a region including a region coding for an amino acid, a region transcribed on RNA at 5' upstream and 3' downstream regions, and further a regulatory region involved in practice and efficiency of transcription and translation outside these regions. The gene derived from *Stenotrophomonas maltophilia* according to the invention is referred to briefly as *Stenotrophomonas maltophilia*-β-lactam acylase (smacy), and an expression polypeptide of the smacy gene is abbreviated as SMACY.

According to one aspect of the present invention, a β-lactam acylase produced by a microorganism belonging to the genus *Stenotrophomonas* is provided. The microorganism belonging to the genus *Stenotrophomonas* is not particularly restricted provided that it has ability for producing a β-lactam acylase. There may be mentioned, for example, *Stenotrophomonas maltophilia*, *Stenotrophomonas acidaminiphila*, *Stenotrophomonas africana*, *Stenotrophomonas nitritireducans*, and the like.

Preferably, a β-lactam acylase produced by the *Stenotrophomonas maltophilia* KNK12A strain is provided.

Moreover, there is provided a protein which comprises an amino acid sequence identical or substantially identical with the amino acid sequence shown under SEQ ID NO:2, a protein in which the amino acid sequence shown under SEQ ID NO:2 is modified after translation and having β-lactam acylase activity, or a protein which comprises an amino acid sequence in which one or a plurality of amino acids in the amino acid sequence shown under SEQ ID NO:2 have undergone deletion, substitution or addition and having β-lactam acylase activity.

Furthermore, there is provided a gene containing a DNA coding for a protein which comprises an amino acid sequence identical or substantially identical with the amino acid sequence shown under SEQ ID NO:2, or a protein which comprises an amino acid sequence in which one or a plurality of amino acids in the amino acid sequence shown under SEQ ID NO:2 have undergone deletion, substitution or addition and having β-lactam acylase activity. The DNA which is of the invention but does not have exactly the same base sequence as SEQ ID NO:1 is also called "DNA mutant" hereinafter.

Said gene is preferably one isolated from a microorganism belonging to the genus *Stenotrophomonas*, and more preferably one isolated from *Stenotrophomonas maltophilia*.

The "substantially identical amino acid sequence" referred to herein represents an amino acid sequence constituting a protein having characteristically the same activity, and having the homology degree with the total amino acid sequence shown under SEQ ID NO:2 of not less than about 80% in total, more preferably about not less than 90%.

Additionally, the term "one or a plurality of amino acids have undergone deletion, substitution or addition" represents that amino acids of the number capable of being deleted, substituted or added by the conventionally known method such as site-directed mutagenesis are deleted, substituted or added.

That is, in the invention, the DNA mutant can be prepared from a DNA comprising the base sequence shown under SEQ ID NO:1 by the known method in the field. As such operation, there may be mentioned, for example, conservative modification modifying the base sequence alone without modifying the amino acid sequence such as site-directed mutagenesis, point mutation, deletion, duplication, inversion, translocation, and degeneracy of a genetic code.

As the above DNA mutant, for example, preferred is a DNA coding for a protein in which the 204th methionine in the amino acid sequence shown under SEQ ID NO:2 is substituted. Among them, more preferred is a DNA coding for a protein in which the 204th methionine in the amino acid sequence shown under SEQ ID NO:2 is substituted with valine. For substituting the 204th methionine with valine in the amino acid sequence shown under SEQ ID NO:2, for example, a DNA in which the 735th adenine is substituted with guanine in the DNA base sequence shown under SEQ ID NO:1 is used.

Furthermore, there is provided a gene which contains a DNA coding for a protein in which the amino acid sequence shown under SEQ ID NO:2 is modified after translation and having β-lactam acylase activity.

Herein, the term "modification after translation" represents a partial deletion or modification of the amino acid sequence after translating mRNA into a protein, and for example, represents one in which a signal sequence required for move of protein to a periplasm region of microorganisms (characterized in being about 20 amino acids at an N-terminal site of protein and being hydrophobic amino acids) is enzymatically deleted.

β-lactam acylase activity refers to hydrolysis (deacylation) activity in the case where an acyl group is detached by water, and as the reversible reaction thereof, transfer activity in the case where the transfer of an acyl group from an activated side chain substrate into a nucleophilic substance is catalyzed. Additionally, in the case of hydrolysis activity, 1 unit refers to an enzyme amount with which hydrolysis of 1 μmole of amoxycillin is catalyzed per minute. In the case of transfer activity, 1 unit refers to an enzyme amount with which 1 μmole of amoxycillin is synthesized per minute. The enzyme amount can be quantitated using HPLC, etc.

Furthermore, the gene of the invention may be a gene which contains a DNA in which the base sequence corresponding to the site coding for the amino acid sequence shown under SEQ ID NO:2 in the base sequence shown under SEQ ID NO:1 codes for the amino acid sequence identical with the amino acid sequence shown under SEQ ID NO:2. That is, the base sequence shown under SEQ ID NO:1 contains a DNA coding for the same amino acid sequence as the amino acid sequence shown under SEQ ID NO:2.

Furthermore, the present invention provides the following polynucleotides. A polynucleotide which contains a base sequence coding for a protein comprising an amino acid sequence identical or substantially identical with the amino acid sequence shown under SEQ ID NO:2, a polynucleotide which contains a base sequence coding for a protein in which the 204th methionine in the amino acid sequence shown under SEQ ID NO:2 is substituted with valine, a polynucleotide which contains a base sequence coding for a protein in which the 204th methionine in the amino acid sequence shown under SEQ ID NO:2 is substituted, a polynucleotide which contains a base sequence coding for a protein comprising an amino acid sequence in which one or a plurality of amino acids in the amino acid sequence shown under SEQ ID NO:2 have undergone deletion, substitution or addition and having β-lactam acylase activity, a polynucleotide which contains a base sequence coding for a protein in which the amino acid sequence shown under SEQ ID NO:2 is modified after translation and having β-lactam acylase activity, a polynucleotide which contains a base sequence in which the base sequence corresponding to the site coding for the amino acid sequence shown under SEQ ID NO:2 in the base sequence shown under SEQ ID NO:1 codes for the amino acid sequence identical with the amino acid sequence shown under SEQ ID NO:2, a polynucleotide which contains the base sequence shown under SEQ ID NO:1, and the above polynucleotide which is isolated from a microorganism belonging to the genus *Stenotrophomonas*.

Furthermore, the protein of the invention may be a protein which comprises an amino acid sequence identical or substantially identical with the amino acid sequence shown under SEQ ID NO:2, a protein which comprises an amino acid sequence in which one or a plurality of amino acids in the amino acid sequence shown under SEQ ID NO:2 have undergone deletion, substitution or addition and having β-lactam acylase activity, or a protein in which the amino acid sequence shown under SEQ ID NO:2 is modified after translation and having β-lactam acylase activity. The protein which is of the invention but does not have exactly the same amino acid sequence as SEQ ID NO:2 is also called "a mutant protein".

In such cases, as the mutant protein, there may be mentioned a protein coded by the DNA mutant as described above, and further a protein in which the fundamental β-lactam acylase activity is not changed but the amino acid sequence is conservatively or semiconservatively modified (for example, substitution of amino acids having an aliphatic chain such as glycine, valine, leucine and isoleicine, or substitution of amino acids having an aromatic chain such as phenylalanine, tyrosine and tryptophan), and the like.

As the above mutant protein, preferred is a protein which comprises an amino acid sequence in which the 204th methionine in the amino acid sequence shown under SEQ ID NO:2 is substituted. Particularly preferred is a protein which comprises an amino acid sequence in which the 204th methionine in the amino acid sequence shown under SEQ ID NO:2 is substituted with valine. In such mutant β-lactam acylase, ester decomposition activity of the substrate D-p-hydroxyphenylglycine methyl ester (HPGOMe) is reduced, and acylase activity is enhanced.

Moreover, the invention provides a gene which contains a transcription regulatory sequence contained in the gene according to the invention, and a gene which contains a translation regulatory sequence. Said transcription regulatory sequence refers to a sequence containing 100 bases upstream site from the 125th in SEQ ID NO:1. Said translation regulatory sequence is a sequence containing 50 bases upstream site from the 125th in SEQ ID NO:1.

Furthermore, the present invention provides a gene under the control of regulon containing a transcription and/or translation regulatory sequence, wherein either or both of said regulatory sequence(s) is (are) substituted with other transcription and/or translation regulatory sequence each obtainable by the same or different living organism.

Herein, the other transcription and/or translation regulatory sequence each obtainable by the same or different living organism is not particularly restricted if the gene of the invention can be expressed therewith, and ones known in the field can be used. Specifically, there may be mentioned general regulatory sequences, etc. derived from *Escherichia coli* and antinomyces.

According to another aspect of the invention, a recombinant vector which comprises at least one of the above gene according to the invention is provided. Furthermore, a transformant which contains said recombinant vector is also provided.

This recombinant vector is prepared by coupling the gene of the invention into a vector for recombination cut with an appropriate restriction enzyme.

As the vector for recombination to be used for producing the recombinant vector of the invention, conventionally known ones can be used. For example, for improving transcription efficiency, there may be mentioned a vector providing lac operon, T7RNA polymerase promoter, etc. to upstream of an insertion gene and having a kanamycin resistance gene, tetracycline resistance gene, etc. as a selective marker.

As the method for preparing the recombinant vector, methods well-known to the person skilled in the art can be employed. For example, a method described in Molecular Cloning (Cold Spring Harbor Laboratory Press, 1989), etc. can be applied.

Moreover, the host to be used in producing a transformant is not particularly restricted, but for example, there may be mentioned a gram-negative microorganism, a gram-positive microorganism, etc. As the gram-negative microorganism, there may be mentioned, for example, those belonging to the genus *Esherichia*, the genus *Psudomonas*, etc., and as the gram-positive microorganism, there may be mentioned, for example, those belonging to the genus *Bacillus* and the genus *Streptmyces*.

As the method for preparing the transformant, methods well-known to the person skilled in the art can be employed. For example, a method described in Molecular Cloning (Cold Spring Harbor Laboratory Press, 1989), etc. can be applied.

As the thus-obtained transformant, specifically, there may be mentioned pUCNTkmTn5-KNK-L/HB101 (accession number; FERM BP-8362, deposit organization; the National Institute of Advanced Industrial Science and Technology International Patent Organism Depositary (Central 6, 1-1-1, Higashi, Tsukuba, Ibaraki, Japan), original deposition date; Oct. 30, 2002), and pUCNT-Tn5-MuKNK-L/HB101 (accession number; FERM BP-8369, deposit organization; the National Institute of Advanced Industrial Science and Technology International Patent Organism Depositary (Central 6, 1-1-1, Higashi, Tsukuba, Ibaraki, Japan), original deposition date; Apr. 23, 2003).

Furthermore, the invention provides a recombinant vector containing a β-lactam acylase gene engineered regarding the above regulatory sequence, and a transformant containing said recombinant vector.

According to another aspect of the invention, the invention provides a method of producing a β-lactam acylase which comprises culturing the above transformant, and recovering a β-lactam acylase produced by said transformant, that is, a method of producing a β-lactam acylase which comprises culturing a transformant coded with a β-lactam acylase or a transformant containing a recombinant vector coded with a β-lactam acylase, and recovering a β-lactam acylase in the isolated form.

Moreover, the invention provides an immobilized β-lactam acylase which is obtainable by culturing the above microorganism or the above transformant, and immobilizing the cell, cell-mixed culture, cell disrupted product, or a β-lactam acylase extracted and purified from the cell.

Furthermore, the invention provides a method of producing a β-lactam acylase in a transformant or of enhancing the production which comprises preparing the above recombinant vector, transforming a host with said recombinant vector, cloning the obtained transformant, and selecting.

By culturing a transformant in a general nutritional medium, the character of an introduced recombinant DNA can be expressed. When the recombinant DNA is provided with characteristics derived from a gene DNA or vector DNA, agents (e.g. kanamycin, neomycin, chloramphenicol, tetracycline, etc.) can be supplemented to the medium according to those characteristics.

For obtaining the thus-obtained transformant as an enzyme source, culture may be carried out using a general medium. However, where necessary, a treatment for enzyme induction such as an addition of IPTG (isopropylthio-β-D-galactoside) can also be carried out.

As a medium which can be used for culturing a transformant, usually, there may be mentioned a general medium containing carbon sources (e.g. carbohydrates such as glucose and sucrose, organic acids such as acetic acid, alcohols, etc.), nitrogen sources (e.g. ammonia gas, ammonia water, ammonium salt, etc.), and inorganic ions (e.g. a phosphate ion, magnesium ion, potassium ion, iron ion, etc.). When organic micronutrients such as a vitamin and an amino acid are added to the medium, a preferable result can be obtained in many cases.

Furthermore, according to another aspect of the invention, as a mode for using said β-lactam acylase enzyme, there may be mentioned a culture of said transformant, cell, cell treatment product, immobilized cell, enzyme extracted from the cell, immobilized enzyme, etc. These can be used in acylation or acyl group conversion processes of large scales.

As the cell treatment product, there may be mentioned, for example, a crude extract, freeze-dried cultured cell, acetone-dried product, lysozyme-treated cell, and ultrasonic-disrupted cell.

For said enzyme-containing solution, a further purification can be carried out by conventional method of isolation or purification of protein, enzyme, etc. For example, the enzyme can be recovered as a precipitate by salt precipitation methods which comprises adding ammonium sulfate, sodium chloride, sodium sulfate, etc., organic solvent precipitation methods which comprises adding acetone, etc., or the like method. Moreover, the enzyme can be purified by combining means of ion exchange chromatography, adsorption chromatography, hydrophobic chromatography, gel filtration chromatography, etc.

The thus-obtained said β-lactam acylase has the distinctive characteristic for hardly showing enzyme inhibition by phenylacetic acid, phenoxyacetic acid, and amoxycillin.

Furthermore, the cell, cell treatment product, cell-free enzyme extract, and purified enzyme can be immobilized by conventional manners. The immobilization can be carried out by the methods well-known to the person skilled in the art such as a crosslinking method, covalent bonding method, physical adsorption method, and entrapment. Additionally, as the immobilization method, for example, the method shown in WO 96/20275 is helpful.

As a support to be used for the immobilization, suited are phenol formaldehyde anion exchange resins such as Duolite A568 or DS17186 (Rohm and Haas Company: registered trademark), polystyrene resins having a functional group of various amines or ammonium salt, e.g. Amberlite IRA935, IRA945 and IRA901 (Rohm and Haas Company: registered trademarks), Lewatit OC1037 (Bayer Company: registered trademark) and Diaion EX-05 (Mitsubishi Chemical Corporation: registered trademark), or various anion exchange resins having a functional group of diethanol amine type. Additionally, supports such as DEAE-cellulose can also be used.

Furthermore, for making the enzyme adsorption stronger and more stabilized, generally, a crosslinking agent is used. As a suitable example, there may be mentioned glutaraldehyde. As for the enzyme to be used, not only a purified enzyme, but also those having various purification degrees such as a cell, cell treatment product and cell-free enzyme extract can be used. For the preparation of the immobilized cell or immobilized enzyme, general preparation methods comprising adding a support to a cell suspension or enzyme solution to make the cell or enzyme adsorb the support, and then carrying out crosslinking treatment, etc.

A β-lactam antibiotic can be synthesized by a method comprising bringing a β-lactam core substrate and a side chain substrate into contact with said enzyme in a medium such as water and a buffer solution. As the side chain substrate to be used in this case, an ester compound and the hydrochloride or amide body thereof can be used. When the β-lactam antibiotic is amoxycillin, the β-lactam core substrate is 6-aminopenicillanic acid (6-APA), and the side chain substrate is D-p-hydroxyphenylglycine methyl ester (HPGOMe), etc.

That is, said reaction can be generally carried out by dissolving or suspending, or by getting through a cell, cell treatment product, cell-free enzyme extract, purified enzyme, or the immobilized product thereof in a medium containing a substrate. This reaction can be carried out by, for example, reacting at 20 to 40° C. for about 30 minutes to 8 hours.

Figure 1:
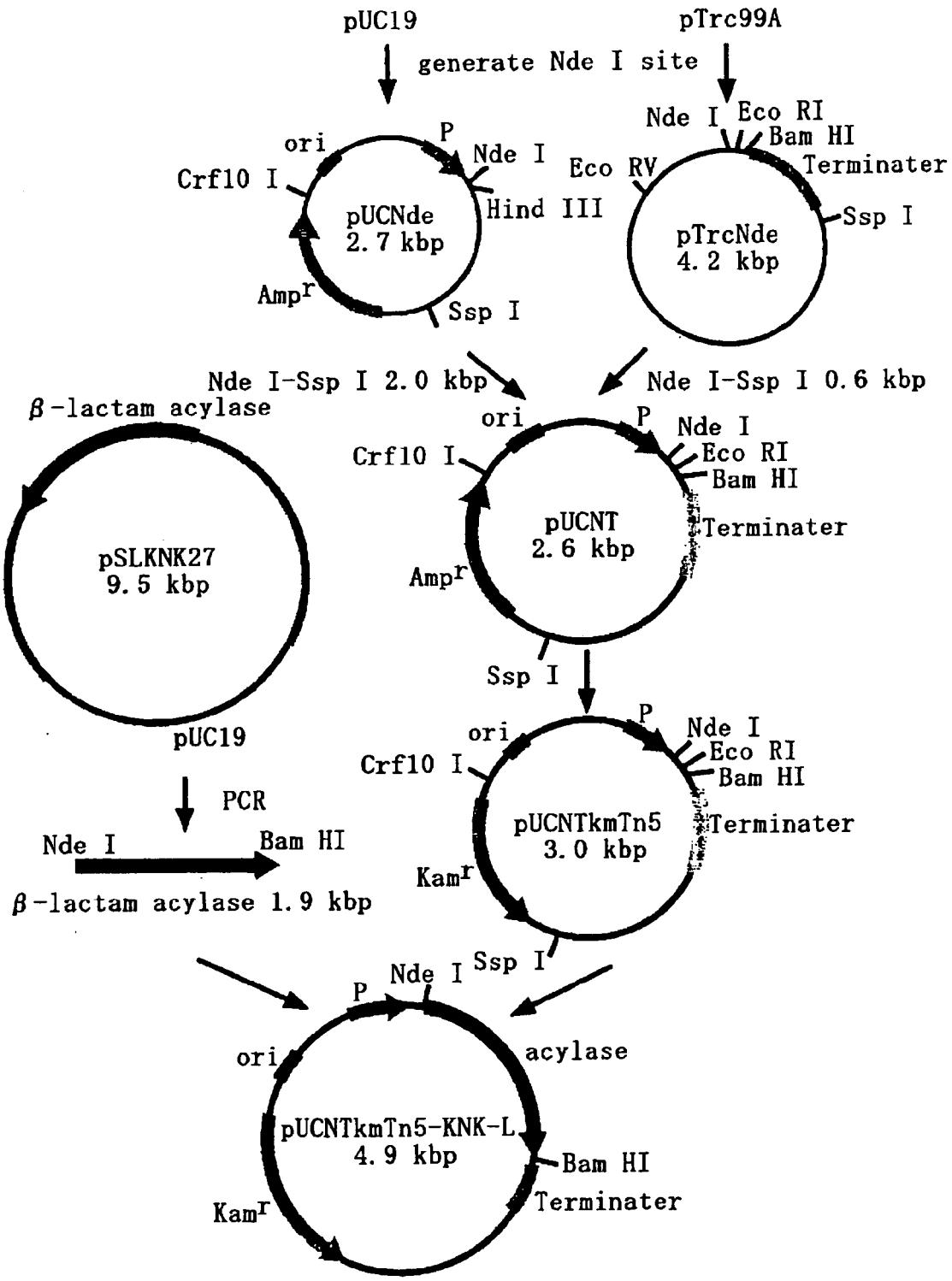
FIG. 1 is a construction view of the β-lactam acylase gene expression vector according to one aspect of the invention carried out in Example 5.

In addition, in the graphs of FIG. 3, FIG. 4, FIG. 5, FIG. 6 and FIG. 7, KNK12A refers to a *Stenotrophomonas maltophilia* KNK12A strain-derived β-lactam acylase, PenG amidase refers to *Escherichia coli*-derived PenG amidase, and the mutant type refers to pUCNT-Tn5-MuKNK-L1/HB101 strain-producing 1 amino acid-substituted mutant β-lactam acylase.

BEST MODE FOR CARRYING OUT THE INVENTION

The following examples further illustrate the present invention in detail. That is, embodiments of the gene of the invention, protein, recombinant vector, transformant, production of β-lactam antibiotic, etc. are explained below. However, the invention is not restricted to the following embodiments.

Material and Method

Cloning of a β-Lactam Acylase Gene

Overall gene manipulation and cloning method were carried out as described in Molecular Cloning (Cold Spring Harbor Laboratory Press, 1989). The enzyme, plasmid, and *E. coli* cloning host used for the DNA manipulation were purchased from market suppliers, and used according to their explanations.

Culture Medium

B culture Medium

Peptone 5 g/l, yeast extract 5 g/l, $K_2HPO_4$ 2 g/l, sucrose 20 g/l, $MgCl_2 \cdot 6H_2O$ 1 g/l, sodium glutamate 2 g/l, $FeSO_4 \cdot 7H_2O$ 0.1 g/l, pH 7.2

LB Culture Medium

Bactotrypton 10 g/l, yeast extract 5 g/l, NaCl 5 g/l, pH 7.0

CM Culture Medium

Meat extract 10 g/l, yeast extract 5 g/l, NaCl 3 g/l, pH 7.0

Buffer Solution

1×SSC 0.15 M NaCl, 0.015 M sodium citrate 30 mM KPB (pH 6.0) 30 mM $KH_2PO_4$, adjusted to pH 6.0 with KOH 50 mM KPB (pH 5.0) 50 mM $KH_2PO_4$, adjusted to pH 5.0 with KOH Strain The *Stenotrophomonas maltophilia* KNK12A strain was used as a donor strain for a β-lactam acylase of *Stenotrophomonas maltophilia*.

*Escherichia coli* DH5α strain and *Escherichia coli* HB101 strain were used as hosts of recombinant plasmid.

*Pseudomonas riboflavina* was used as a bioassay strain.

β-Lactam Acylase Activity

β-lactam acylase activity refers to hydrolysis (deacylation) activity in the case where an acyl group is detached by water, and as the reverse reaction thereof, transfer activity in the case where the transfer of an acyl group from an activated side chain substrate into a nucleophilic substance is catalyzed.

In the case of hydrolysis activity, 1 unit refers to an enzyme amount with which hydrolysis of 1 μmole of amoxycillin is catalyzed per minute.

In the case of transfer activity, 1 unit refers to an enzyme amount with which 1 μmole of amoxycillin is synthesized per minute.

The reaction conditions are as follows, and quantitation was carried out by HPLC.

Decomposition Reaction of Amoxycillin

To 200 μl of a solution prepared by dissolving amoxycillin in 30 mM KPB (pH 6.0) at the concentration of 0.5%, 10 μl of the enzyme solution obtained in (Examination Example 1) was added. The mixture was subjected to reaction for 1 hour while shaking at 30° C., and 1N HCl was added in 1/20 amount of the substrate solution to terminate the reaction.

Amoxycillin Synthesis Reaction 6-aminopenicillanic acid (6-APA) and HPGOMe-HCl were dissolved in 30 mM KPB (pH 6.0) at the concentration of 0.5% to prepare a substrate solution. Cells or crude enzyme solution was suspended in the substrate solution, and the suspension was subjected to reaction for 4 hours at 30° C. while shaking. Then, 1N HCl was added thereto in 1/20 amount of the substrate solution to terminate the reaction.

D-p-Hydroxyphenylglycine Methyl Ester (HPGOMe) Hydrolysis Reaction

HPGOMe-HCl was dissolved in 30 mM KPB (pH 8.0) at the concentration of 0.5% to prepare a substrate solution. Cells or crude enzyme solution was suspended in the substrate solution, and the suspension was subjected to reaction for 4 hours at 30° C. while shaking. Then, 1N HCl was added thereto in 1/20 amount of the substrate solution to terminate the reaction.

Detection Using Thin Layer Chromatography (TLC)

Amoxycillin in the cell reaction and crude enzyme reaction was detected using thin layer chromatography. A reaction solution was centrifuged to recover the supernatant, and a trace amount thereof was spotted on a silica gel thin layer plate to be developed with a development solvent comprising ethyl acetate:acetic acid:water=60:20:20. After removal of the solvent, amoxycillin was detected by a ninhydrin reaction.

Detection Using High-Performance Liquid Chromatography (HPLC)

A reaction solution was centrifuged to recover the supernatant, and determined using HPLC by diluting to 10-fold with a mobile phase. The analysis conditions were as follows. Column: Cosmosil 5C18 AR (Nacalai Tesque, Inc.), mobile phase: 1% acetonitrile/50 mM KPB (pH 5.0), flow rate: 1.0 ml/min, column temperature 35° C., and determination wavelength: 225 nm. The peak was identified using a standard product, and amoxycillin trihydrate (Wako Pure Chemical Industries, Ltd.) was used as the standard product of amoxycillin. The retention time was 1.8 min for HPG, 5.9 min for 6-APA, 7.5 min for amoxycillin, and 9.4 min for HPGOMe-HCl.

EXAMPLE 1

Purification of a β-Lactam Acylase of the *Stenotrophomonas maltophilia* KNK12A Strain Using B culture medium, the KNK12A strain was proliferated at 30° C. The following operations were carried out at 4° C. Cells were recovered by centrifugation, suspended in 0.1 M Tris-HCl (pH 8.0), 4.7 g/l of EDTA-2Na and 0.13 g/l of lysozyme were added thereto, and the mixture was stirred overnight. $MgSO_4$-$7H_2O$ and bovine pancreatic deoxyribonuclease I were added to the mixture at the concentrations of 3.13 g/l and 0.06 mg/l, respectively, and the resultant was subjected to reaction overnight. The cells were disrupted by ultrasonic wave, and the supernatant was recovered by centrifugation. $Ca(CH_3COO)_2$—$H_2O$ and $KH_2PO_4$ were added at the both concentrations of 22.9 g/l, and the supernatant was recovered by centrifugation. After the dialysis, purification was carried out using a cation exchange gel chromatograph (CM Sepharose CL-6B) for 3 times, and gel filtration chromatograph (Sephacryl-300) once (Agric. Biol. Chem., 44(5), 1069, 1980). The fraction eluted from the column was observed to have amoxycillin synthesis activity by TLC, and the subsequent purification step followed. The obtained SMACY protein showed a molecular weight of about 70 kDa by SDS-PAGE.

EXAMPLE 2

Determination of the Amino Acid Sequence of a β-Lactam Acylase of the *Stenotrophomonas maltophilia* KNK12A Strain SMACY protein obtained in the above purification method (Example 1) was subjected to partial decomposition with lysyl endopeptidase, and the amino acid sequence of the peptide fragment was determined. SMACY protein was suspended in a buffer (10 mM Tris-HCl (pH 9.0), 4 M Urea). Thereto was added with lysyl endopeptidase in an amount of ⅕₀ to SMACY protein, and the mixture was subjected to reaction at 37° C. for 6 hours. Peptides were fractioned by a reverse phase column (YMC-Pack PROTEIN-RP (YMC Co., Ltd)), and analyzed with Model 49x protein sequencer (Applied Biosystems). The obtained amino acid sequence is shown under SEQ ID NO:3.

EXAMPLE 3

Cloning of a β-Lactam Acylase Gene of the *Stenotrophomonas maltophilia* KNK12A Strain A fraction of 6 to 8 kbp obtained by isolating a genome DNA of the *Stenotrophomonas maltophilia* KNK12A strain and digesting with NcoI was cloned to pSL301 plasmid (Invitrogen Corporation) treated with NcoI and alkali phosphatese (CIAP). The resultant was transformed into *Escherichia coli* HB101 strain and sown in an L-Amp plate (LB culture medium added with 15 g/l of bactoagar and 50 mg/l of ampicillin), and cultured at 37° C. overnight. The colony of this plate was replicated to a nylon membrane, cultured until the colony became an appropriate size, and the cells were dissolved to produce a filter. Then, colony hybridization was carried out in the amino acid sequence shown under SEQ ID NO:3 using K1 oligonucleotide shown under SEQ ID NO:4 coding for the amino acid sequence shown under SEQ ID NO:5 as a probe. The 3'-terminal of K1 oligonucleotide was fluorescence-labeled with Gene Images 3'-oligo-labelling (Amersham Pharmacia Biotech, Inc.), and hybridized overnight in a hybridization buffer at 50° C. (5×SSC, 0.1% sodium dodecyl sulfate, 20-fold dilution liquid block (Amersham Pharmacia Biotech, Inc.), 0.5% dextran sulphate). The membrane was washed in a 5×SSC solution at room temperature (0.1% sodium dodecyl sulfate), and subsequently in a 1×SSC solution at 42° C. (0.1% sodium dodecyl sulfate) and subjected to detection with Gene Images CDP-Star detection module (Amersham Pharmacia Biotech, Inc.) to obtain a positive clone. The plasmid obtained by this clone was named pSLKNK27. This pSLKNK27 was being inserted with a genome fragment of about 6.3 kbp.

EXAMPLE 4

Sequence Determination of a β-Lactam Acylase Gene

The sequence of the positive clone obtained above was subjected to sequencing reaction by deoxy sequence determination using BigDye Terminator Cycle Sequencing FS Ready Reaction Kit (Applied Biosystems), and analyzed with ABI PRISM 310 Genetic Analyzer (Applied Biosystems). The obtained β-lactam acylase gene sequence was shown under SEQ ID NO:1, and the estimated amino acid sequence was shown under SEQ ID NO:2.

EXAMPLE 5

Construction of an Expression Vector of a β-Lactam Acylase Gene

A primer producing Nde I site at the initiation codon site of lac Z gene of pUC19 plasmid was produced, and a polymerase chain reaction (PCR) was carried out to produce pUCNde plasmid which is added with one Nde I site to pUC19 plasmid. PCR was carried out in the same manner on pTrc99A (Amersham Pharmacia Biotech, Inc.) plasmid, and pTrcNde plasmid in which Nco I site was changed to Nde I site was produced. pUCNT plasmid was produced by carrying out ligation of a 2.0 kbp fragment obtained by cutting pUCNde plasmid with Nde I and Ssp I, and a 0.6 kbp fragment obtained by cutting pTrcNde plasmid with Nde I and Ssp I (Journal of Bioscience and Bioengineering, 87, 149, 1999, WO 94/03613).

pUCNTkmTn5 (kam$^r$) plasmid was produced by producing a 1.8 kbp fragment obtained by cutting pUCNT plasmid with Crf10 I and Ssp I, and a 1.2 kbp fragment obtained by PCR of a kanamycin resistance gene using pKC7 plasmid (Gene, 7, 79, 1979) as a template so as to have Crf10 I and Ssp I sites, and subjecting the fragments to ligation.

Next, using pSLKNK27 as a template, PCR was carried out using K-Nde I-4 primer (SEQ ID NO:6 GGAATTC-CATATGCATGTGCGTGCCGTAGC) and K-BamH I-1 primer (SEQ ID NO:7 CGCGGATCCTCAGTACACCG-GCAGGTC) to amplify the β-lactam acylase structural gene fragment. This DNA fragment was cloned to NdeI site and BamHI site of pUCNTkmTn5 (kam$^r$) plasmid vector, and the resultant was named pUCNTkmTn5-KNK-L. The construction view of this expression vector is shown in FIG. 1.

EXAMPLE 6

Expression of a β-Lactam Acylase Gene

A strain prepared by transforming pUCNTkmTn5-KNK-L plasmid into *E. coli* HB101 (pUCNTkmTn5-KNK-L/HB101) was sown in an LB culture medium which has been added with kanamycin at the concentration of 50 mg/l, and the medium was cultured at 30° C. overnight. The cells were recovered by centrifugation and suspended in 30 mM KPB, the supernatant was recovered by centrifugation to carry out SDS-PAGE. Then, a band of about 70 kDa was observed and the expression of β-lactam acylase was confirmed.

EXAMPLE 7

Confirmation of β-Lactam Acylase Activity

The pUCNTkmTn5-KNK-L/HB101 strain was cultured overnight in the same manner as in (Example 6), IPTG was added thereto so as to be 1 mM, and further cultured for 3 hours. The cells were treated on ice with 0.44 mg/ml of lysozyme for 15 minutes, and the supernatant obtained by ultrasonic disruption and centrifugation was referred to as a crude enzyme solution. The total protein mass of the crude enzyme solution was quantitated by the Bradford method. 25 μg of protein was added to 200 μl of a substrate (0.5% HPGOMe-HCl, 0.5% 6-APA). The mixture was subjected to reaction while shaking at 30° C. for 1 hour, and diluted to 10-fold. Then, 10 μl of the mixture was analyzed by HPLC, and the peak of amoxycillin was detected. Thereby, it was confirmed that the *Stenotrophomonas maltophilia* KNK12A strain β-lactam acylase gene cloned to pUCNTkmTn5 plasmid was expressed in the *Escherichia coli* HB101 strain, and had activity.

EXAMPLE 8

Purification of a β-Lactam Acylase

As in (Example 1), the pUCNTkmTn5-KNK-L/HB101 strain was cultured, subjected to cell disruption, and the supernatant was recovered by centrifugation. This supernatant was filtered with a 0.45 μm filter, and cation exchange gel chromatograph was carried out using AKTA explorer 10S system (Amersham Pharmacia Biotech, Inc.). The fraction eluted from the column was confirmed to have amoxycillin synthesis activity by TLC. SDS-PAGE was carried out for the fraction showing amoxycillin synthesis activity, and then it was confirmed that the purification proceeded to such the stage that β-lactam acylase occupied not less than 10% of the total protein. Thus, the following characteristics were examined using this fraction.

EXAMINATION EXAMPLE 1

Comparison of Amoxycillin Synthesis Activity

Amoxycillin synthesis activities of the *Stenotrophomonas maltophilia* KNK12A strain-derived β-lactam acylase and the known *Escherichia coli* PenG amidase (Sigma) were compared. As an enzyme solution, the fraction obtained in (Example 8) (enzyme concentration: about 3.2 ng/10 μl) was used for the *Stenotrophomonas maltophilia* KNK12A strain-derived β-lactam acylase, and 100-fold diluted solution (10.2 munit/10 μl, enzyme concentration: about 3.5 ng/10 μl) was used for *Escherichia coli* PenG amidase.

Figure 3:
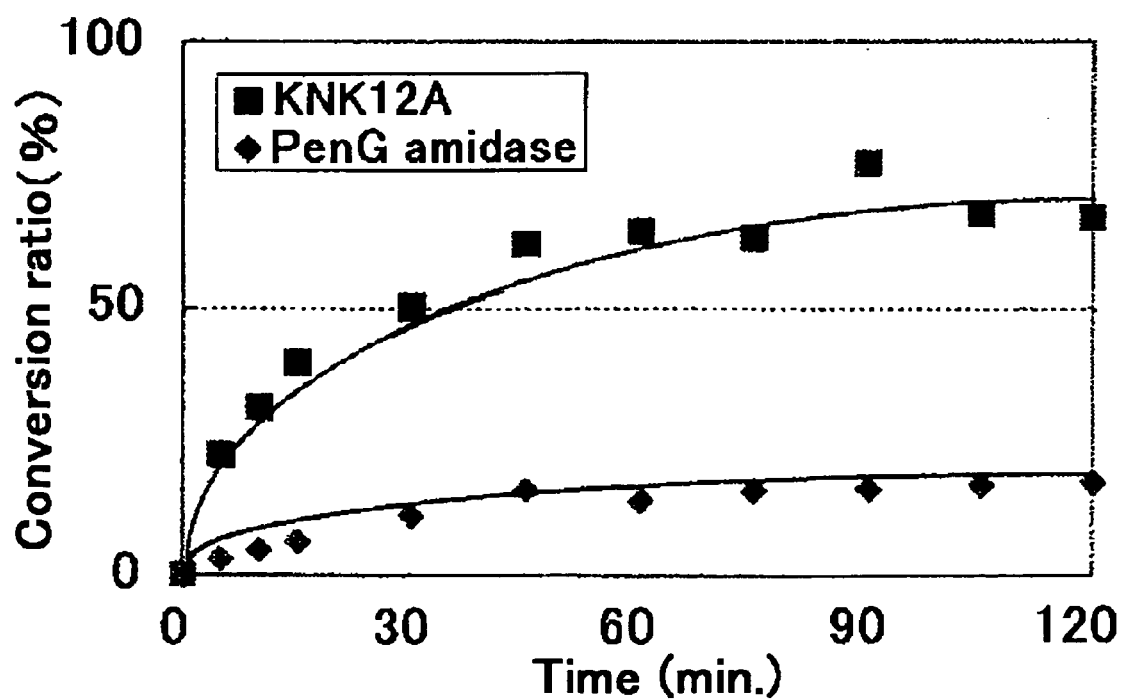
FIG. 3 is a graph showing a comparison result of the synthetic activity of amoxycillin carried out in Examination Example 1.

To 200 μl of a substrate solution prepared by dissolving 6-APA and HPGOMe-HCl in 30 mM KPB (pH 6.0) at the concentration of 0.5%, 10 μl of the enzyme solution was added and the mixture was subjected to reaction while shaking at 30° C. After the lapse of 0, 5, 10, 15, 30, 45, 60, 75, 90, 105 and 120 minutes from the start of the reaction, 1N HCl was added in 1/20 amount of the substrate solution to terminate the reaction. The generated amoxycillin was detected using HPLC. The result is shown in FIG. 3.

From the result, it was found that the *Stenotrophomonas maltophilia* KNK12A strain-derived β-lactam acylase synthesizes amoxycillin at a very high conversion rate as compared with *Escherichia coli* PenG amidase.

EXAMINATION EXAMPLE 2

Comparison of Synthetic Activity Inhibition by Phenylacetic Acid (PAA) and Phenoxyacetic Acid (PXA)

To 200 μl of a substrate solution prepared by dissolving 6-APA and HPGOMe-HCl in 30 mM KPB (pH 6.0) at the concentration of 0.5%, 10 μl of the enzyme solution obtained in (Examination Example 1) was added. PAA was added to be 0.3% and PXA was added to be 0.35%, and the mixture was subjected to reaction while shaking at 30° C. for 1 hour. Then, 1N HCl was added in 1/20 amount of the substrate to terminate the reaction. The generated amoxycillin was detected using HPLC. The result showing relative activity for the respective enzymes with the amoxycillin synthesis amount reacted by the substrate alone being set at 100% is shown in Table 1.

TABLE 1

|   | KNK12 strain-derived β-lactam acylase | *E. coli* PenG amidase |
| --- | --- | --- |
| Substrate | 100% | 100% |
| Substrate + 0.3% PAA | 107% | 0% |
| Substrate + 0.35% PXA | 76% | 0% |

From the result, it was found that the amoxycillin synthesis of *Escherichia coli* PenG amidase is inhibited by phenylacetic acid or phenoxyacetic acid, but that of the *Stenotrophomonas maltophilia* KNK12A strain-derived β-lactam acylase is not inhibited at all, or even in the case there is inhibition, it is slight.

EXAMINATION EXAMPLE 3

Decomposition Activity of Amoxycillin

Figure 4:
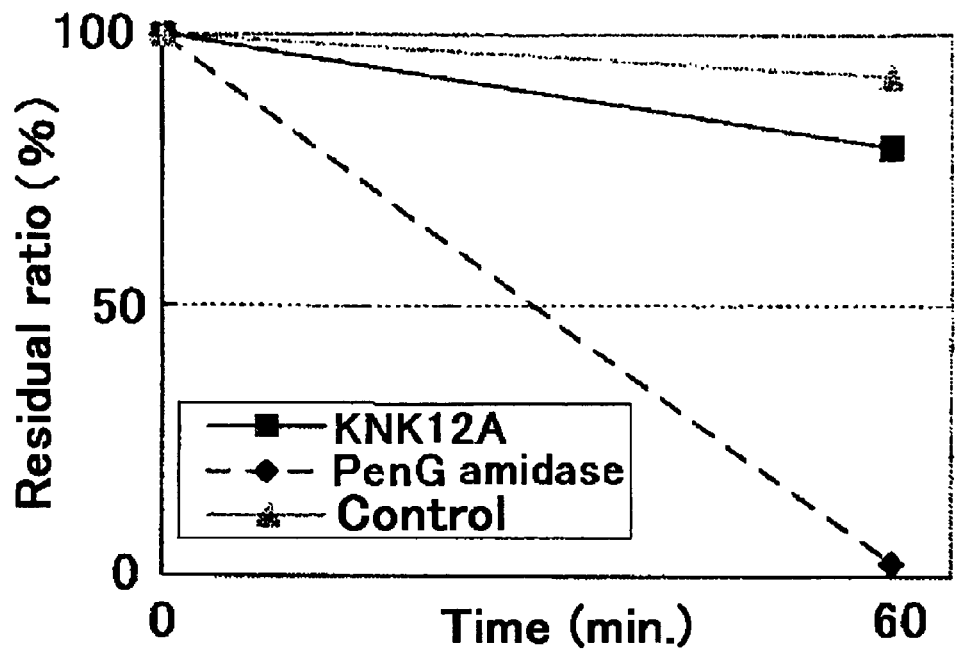
FIG. 4 is a graph showing a comparison result of the decomposition activity of amoxycillin carried out in Examination Example 3.

To 200 μl of a liquid prepared by dissolving amoxycillin in 30 mM KPB (pH 6.0) at the concentration of 0.5%, 10 μl of the enzyme solution obtained in (Examination Example 1) was added. The mixture was subjected to reaction while shaking at 30° C. for 1 hour, and then 1N HCl was added in 1/20 amount of the substrate solution to terminate the reaction. The remained amoxycillin was detected using HPLC. The result is shown in FIG. 4.

From the result, it was found that while *Escherichia coli* PenG amidase decomposes amoxycillin very quickly, the amoxycillin decomposition speed of *Stenotrophomonas maltophilia* KNK12A strain-derived β-lactam is slow.

EXAMINATION EXAMPLE 4

Comparison of Decomposition Activity of HPGOMe

Figure 5:
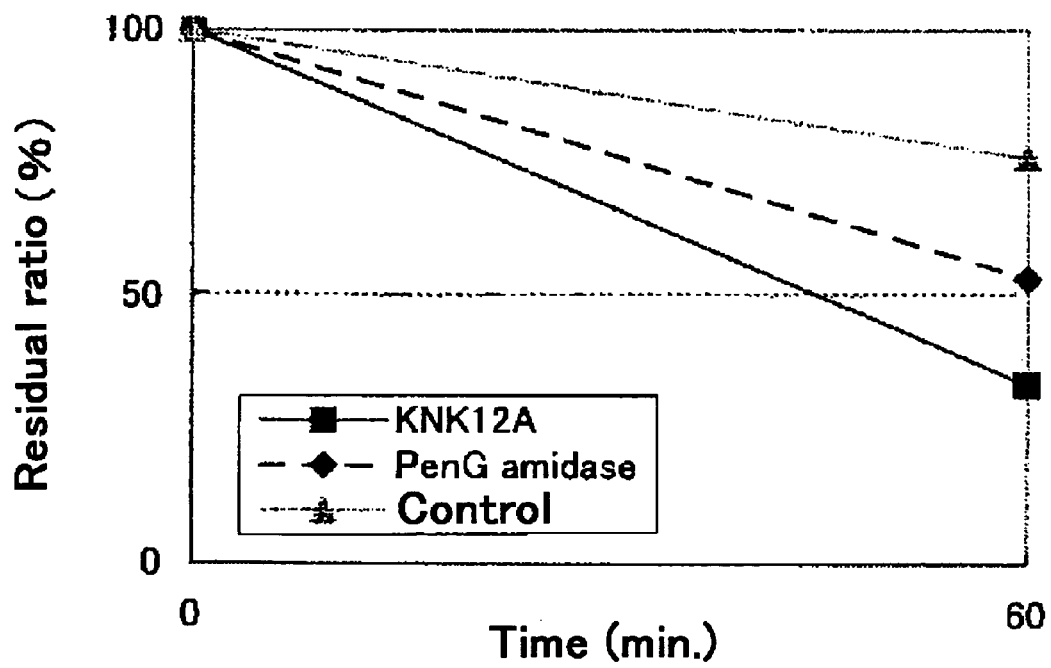
FIG. 5 is a graph showing a comparison result of the decomposition activity of D-p-hydroxyphenylglycine methyl ester (HPGOMe) carried out in Examination Example 1.

To 200 μl of a liquid prepared by dissolving HPGOMe-HCl in 30 mM KPB (pH 6.0) at the concentration of 0.5%, 10μ of the enzyme solution obtained in (Examination Example 1) was added, and the mixture was subjected to reaction while shaking at 30° C. for 1 hour. Then, 1N HCl was added in ½0 amount of the substrate solution to terminate the reaction. The remained HPGOMe was detected using HPLC. The result is shown in FIG. 5.

From the result, the decomposition speed of HPGOMe of the *Stenotrophomonas maltophilia* KNK12A strain-derived β-lactam acylase is faster than that of *Escherichia coli* PenG amidase.

EXAMPLE 9

Immobilization of a β-Lactam Acylase to Resin

In the same manner as in (Example 7), pUCNTkmTn5-KNK-L/HB101 strain was cultured and subjected to cell disruption treatment to prepare a crude enzyme solution. Thereto was added with Duolite A-568 (Rohm and Haas Company) equilibrated with 0.1 M KPB (pH 7.0) in such an amount that the resin was to be 1 g relative to the total protein mass 40 mg. The mixture was stirred at 4° C. for 20 hours under the condition sealed with nitrogen to be adsorbed. After washing this adsorbent resin with 0.1 M KPB (pH 7.0) and 10 mM dithiothreitol (DTT), the protein was crosslinked by reacting with 0.2% glutaraldehyde and 0.1 M KPB (pH 7.0) at 4° C. for 10 minutes to produce an immobilized resin. Relative to 200 μl of a substrate (0.5% HPGOMe-HCl, 0.5% 6-APA), 1 mg of this resin was added and the mixture was subjected to reaction while shaking at 30° C. for 4 hours. Then, the mixture was diluted to 10-fold, and 10 μl of the resultant was analyzed by HPLC to detect the amoxycillin peak.

EXAMPLE 10

Production of a Random-Mutated Acylase Enzyme Recombinant Library

Using pUCNTkmTn5-KNK-L plasmid as a template, PCR was carried out using MT-197 primer (SEQ ID NO:8 AAAAAGCAGGCTGGCACGACAGGTTTC-CCGACTGGA) and MT-198 primer (SEQ ID NO:9 AGAAAGCTGGGTGGATCCTCAGTACAC-CGGCAGGTCGA). For the reaction, Diversify PCR Random Mutagenesis Kit (BD Biosciences Clontech) was used. To 0.2 ml of a microtube, 1 ng of the template and each 10 pmole of primers were added. To the kit, 5 μl of an auxiliary buffer, 1 μl of Diversify dNTP Mix, and TITANIUM Taq Polymerase were added. Additionally, by changing the addition amounts of 8 mM MnSO$_4$ solution and 2 mM dGTP solution from 0 to 4 μl and from 1 to 5 μl, respectively, the number of random mutant was adjusted to 2.0 to 8.1 per length of 1 kbp. After the reaction liquid amount was adjusted to 50 μl by adding sterilized water, 25 cycles of reaction at 94° C. for 30 seconds and at 68° C. for 2 minutes were carried out to conduct DNA amplification and mutagenesis.

Using the random-mutated DNA as a template, PCR was carried out using attB1 primer (SEQ ID NO:10 GGGGA-CAAGTTTGTACAAAAAAGCAGGCT) and attB2 primer (SEQ ID NO:11 GGGGACCACTTTGTACAA-GAAAGCTGGGT) according to conventional manners. 130 ng of the obtained DNA fragment, 300 ng of pDONR (Invitrogen Corporation) attached to Gateway Cloning System (Invitrogen Corporation), 4 μl of buffer, and 4 μl of BP Clonase were mixed, the reaction liquid amount was adjusted to 20 μl with sterilized water, and subjected to reaction at 25° C. for 1 hour. Then, 2 μl of Proteinase K was added to carry out reaction at 37° C. for 10 minutes.

EXAMPLE 11

Screening of a Random Mutant Strain

*E. coli* DH5α was transformed at the random-mutated DNA library and sown in an LB agar plate medium added with kanamycin at the concentration of 25 mg/L, at such rate that about 100 colonies are contained per one plate. Then, the medium was subjected to standing culture at 37° C. overnight. The generated colonies were replicated on two kanamycin-containing CM agar plate media by velvet, and further subjected to standing culture at 37° C. overnight. On one of the replicated plate, a medium prepared by mixing 0.02% HPGOMe-HCl, 0.01% 6-APA, and 0.3% *Pseudomonas riboflavina* CM culture medium cultured overnight with 7 ml CM soft agar culture medium kept warmed at 42° C. was piled up, and the resultant was solidified and subjected to standing culture at 28° C. overnight. The colony where the growth inhibition circle of *Pseudomonas riboflavina* appeared was referred to as a positive strain on which amoxycillin was generated.

The positive strain was inoculated on 10 ml of CM culture medium from the replica plate, and the medium was cultured with shaking at 37° C. overnight. From 2 ml of the culture, cells were recovered by centrifugation, suspended in 30 mM KPB (pH 6.0), and then mixed with 1 ml of a substrate (prepared by dissolving 0.5% HPGOMe-HCl and 0.5% 6-APA in 30 mM KPB, and adjusting to pH 6.0). The mixture was subjected to reaction at 30° C. for 1 hour. 50 μl of 1N HCl was added to terminate the reaction, the supernatant obtained by centrifugation was diluted to 25-fold with 30 mM KPB, and 10 μl thereof was analyzed by HPLC. Among several myriads of mutants, a mutant 0902-2-1 was obtained which has the generated amoxycillin/by-product HPG ratio being improved about twice as compared with that of the control recombinant β-lactam acylase-producing strain pUCNTkmTn5-KNK-L/HB101 strain. The plasmid contained in the obtained mutant was prepared by the general alkali method. The sequencing reaction was carried out using BigDye Terminator Cycle Sequencing FS Ready Reaction Kit (Applied Biosystems), and the sequence was analyzed using ABI PRISM 310 Genetic Analyzer (Applied Biosystems). From the obtained base sequence information, in the β-lactam acylase structural gene shown under SEQ ID NO:1, mutation of the 735th adenine to guanine became clear, and mutation of the 204th methionine of the amino acid sequence shown under SEQ ID NO:2 to valine also became clear.

EXAMPLE 12

Production of a Mutant Acylase Expression Vector

Using the plasmid contained in the mutant 0902-2-1 strain as a template, PCR was carried out using MT-216 primer (SEQ ID NO:12 CGCCTCTAGAAGCGATTCGCCGCG-CATGCGCGACC) and MT-219 primer (SEQ ID NO:13

GCACAAGCTTCTTCCACCAGGTCAGCTGG). The obtained DNA fragment of about 570 bp was completely digested by restriction enzymes XbaI and HindIII.

On the other hand, using pUCNTkmTn5-KNK-L plasmid as a template, PCR was carried out using MT-217 primer (SEQ ID NO:14 TCGCTTCTAGAGGCGCGGCCGGCAG-CATCGTAGGGC) and MT-218 primer (SEQ ID NO:15 GGAAGAAGCTTGTGCAGCACCCGGCC). The obtained DNA fragment of about 4.4 kbp was completely digested by an restriction enzyme XbaI, and partially digested by HindIII.

Figure 2:
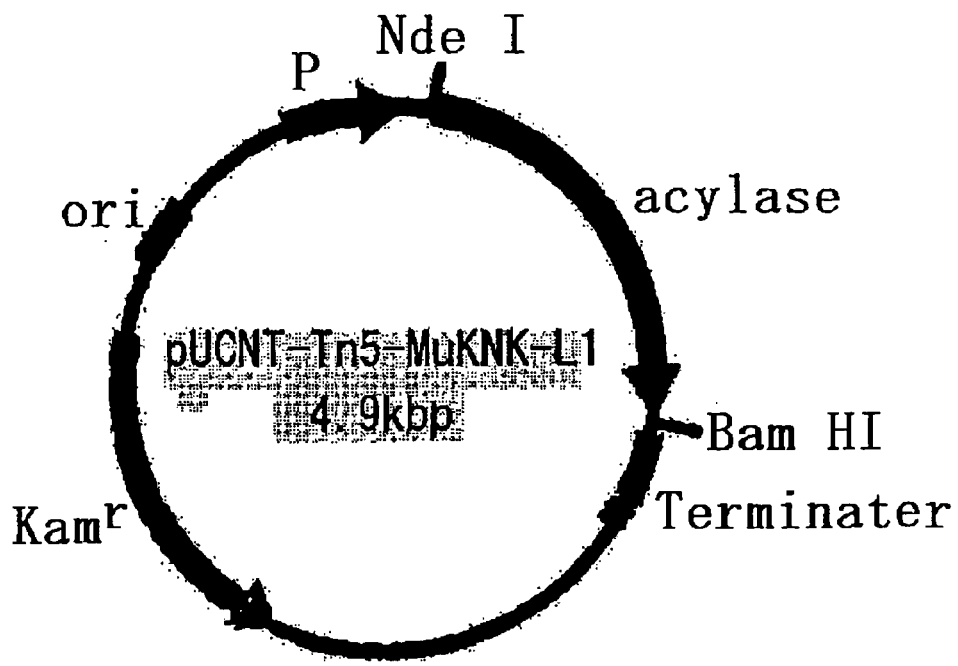
FIG. 2 is a view of the mutant β-lactam acylase gene expression vector of the invention constructed in Example 12.

Both were mixed, and the ligation reaction was carried out to transform *Escherichia coli* HB101. A plasmid was prepared by an alkali method from the obtained kanamycin resistance colony, and a mutant plasmid pUCNT-Tn5-MuKNK-L1 was produced coding for a 1 amino acid-substituted mutant acylase gene. This expression vector is shown in FIG. 2.

EXAMPLE 13

Capability Comparison Examination of a Mutant Acylase

Figure 6:
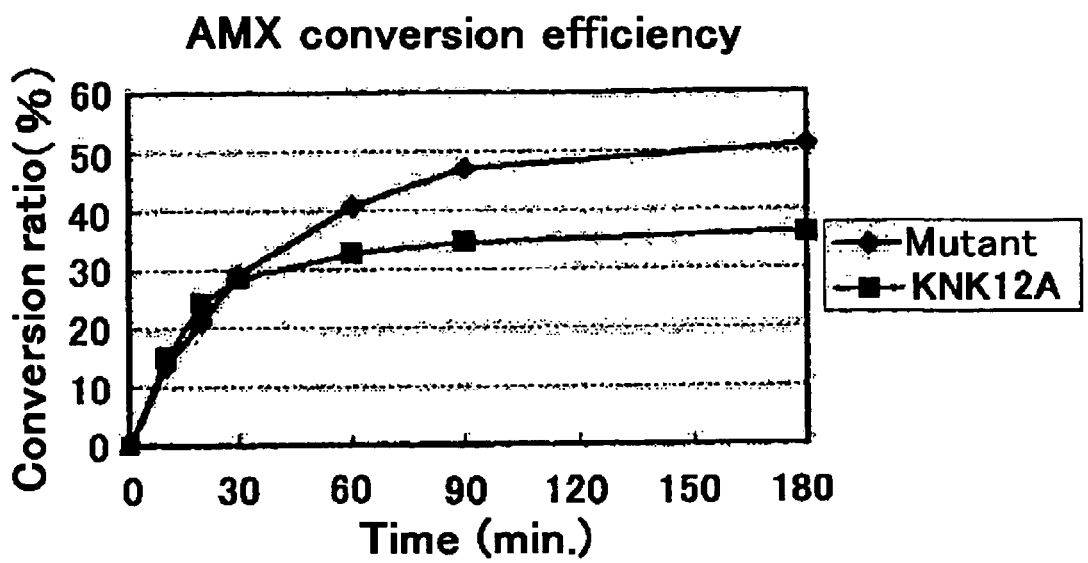
FIG. 6 is a graph showing a comparison result of the synthetic activity of amoxycillin in the mutant β-lactam acylase carried out in Example 13.
Figure 7:
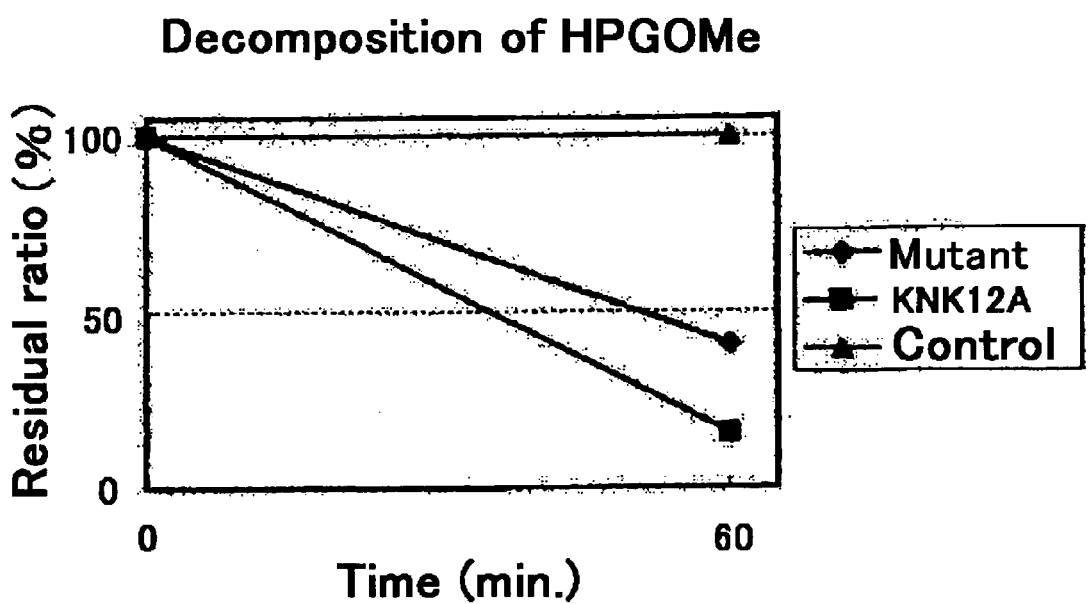
FIG. 7 is a graph showing a comparison result of the ester decomposotion activity of D-p-hydroxyphenylglycine methyl ester (HPGOMe) carried out in Example 13.

A β-lactam acylase-producing strain pUCNTkmTn5-KNK-L/HB101 strain and 1 amino acid-substituted mutant β-lactam acylase-producing strain pUCNT-Tn5-MuKNK-L1/HB101 strain were inoculated in 10 ml of CM culture medium, and shaking culture was carried out at 37° C. overnight. Cells were recovered from 2 ml of the culture by centrifugation, and suspended in 30 mM KPB (pH 6.0). Then, 1 ml of a substrate (prepared by dissolving 0.5% HPGOMe-HCl and 0.5% 6-APA in 30 mM KPB and adjusted to pH 6.0) was mixed therewith, and the mixture was subjected to reaction at 30° C. After the lapse of 10, 20, 30, 60, 90 and 180 minutes from the start of the reaction, 1N HCl was added in 1/20 amount of the substrate solution to terminate the reaction. Then, the centrifuged supernatant was diluted to 25-fold with 30 mM KPB, and 10 μl thereof was analyzed by HPLC. The amoxycillin conversion efficiency comparison is shown in FIG. 6, and ester decomposition degree comparison of D-p-hydroxyphenylglycine methyl ester (HPGOMe) is shown in FIG. 7.

INDUSTRIAL APPLICABILITY

By bonding a β-lactam acylase gene belonging to the genus *Stenotrophomonas* or the modified gene thereof obtainable by reducing substrate decomposition activity and enhancing acylase activity to an expression vector to express those genes in the host, a β-lactam acylase or the modified β-lactam acylase can be efficiently prepared. This β-lactam acylase or modified β-lactam acylase can be used in the process of deacylation/acyl group conversion in a great amount, and for example, can be used for enzymatic production method of amoxycillin.

The invention claimed is:

1. An isolated and purified gene which contains a DNA encoding a protein comprising the amino acid sequence shown under SEQ ID NO: 2.

2. An isolated and purified gene which contains a DNA encoding a protein comprising the amino acid sequence shown under SEQ ID NO: 2, in which the 204$^{th}$ methionine in the amino acid sequence shown under SEQ ID NO:2 is substituted with valine.

3. The gene according to claim 1 which is isolated from a microorganism belonging to the genus *Stenotrophomonas*.

4. An isolated and purified polynucleotide which contains a nucleotide sequence encoding a protein consisting of the amino acid sequence shown under SEQ ID NO: 2.

5. An isolated and purified polynucleotide which contains a nucleotide sequence encoding a protein consisting of the amino acid sequence shown under SEQ ID NO: 2, in which the 204$^{th}$ methionine in the amino acid sequence shown under SEQ ID NO: 2 is substituted with valine.

6. An isolated and purified polynucleotide which contains the nucleotide sequence shown under SEQ ID NO: 1.

7. The polynucleotide according to claim 4 which is isolated from a microorganism belonging to the genus *Stenotrophomonas*.

8. An isolated and purified protein which comprises the amino acid sequence shown under SEQ ID NO: 2.

9. An isolated and purified protein which comprises the amino acid sequence shown under SEQ ID NO: 2, in which the 204$^{th}$ methionine in the amino acid sequence shown under SEQ ID NO: 2 is substituted with valine.

10. An isolated and purified gene which contains a transcription regulatory sequence contained in the gene according to claim 1, wherein the transcription regulatory sequence is a sequence containing the 100 nucleotides upstream from the 125$^{th}$ residue in SEQ ID NO: 1.

11. An isolated and purified gene which contains a translation regulatory sequence contained in the gene according to claim 1, wherein the translation regulatory sequence is a sequence containing the 50 nucleotides upstream from the 125$^{th}$ residue in SEQ ID NO: 1.

12. The gene according to claim 1 under the control of a transcription and/or translation regulatory sequence, wherein either or both of said transcription and/or translation regulatory sequence(s) is (are) substituted with other transcription and/or translation regulatory sequence from the same or different living organism.

13. A recombinant vector which comprises the gene according to claim 1.

14. A transformed microorganism
which is obtained by transforming a host microorganism with the recombinant vector according to claim 13.

15. The transformed microorganism according to claim 14, wherein the host microorganism is a gram-negative microorganism.

16. The transformed microorganism according to claim 14, wherein the host microorganism is a gram-positive microorganism.

17. The transformed microorganism according to claim 14, wherein the transformed microorganism is FERM BP-8362.

18. The transformed microorganism according to claim 14, wherein the transformed microorganism is FERM BP-8369.

19. A method of producing a β-lactam acylase
which comprises culturing the transformed microorganism according to claim 14, and recovering a β-lactam acylase produced by said transformed microorganism.

20. An isolated and purified β-lactam acylase which comprises an amino acid sequence encoded by the polynucleotide according to claim 4.

21. A method of producing a β-lactam acylase in a transformed microorganism or of enhancing the production
which comprises preparing the recombinant vector according to claim 13, transforming a host microorganism with said recombinant vector, culturing the obtained transformed microorganism, and isolating said β-lactam acylase.

22. A method of producing a β-lactam antibiotic by bringing a β-lactam core substrate and a side chain substrate into contact with the β-lactam acylase according to claim 20.

23. The method according to claim 22, wherein the β-lactam antibiotic is amoxycillin.

24. An immobilized β-lactam acylase which is obtained by culturing the transformed microorganism according to claim 14, and immobilizing the β-lactam acylase extracted and/or purified from the transformed microorganism.

* * * * *

UNITED STATES PATENT AND TRADEMARK OFFICE
CERTIFICATE OF CORRECTION

PATENT NO.        : 7,195,892 B2                                    Page 1 of 1
APPLICATION NO.   : 10/516587
DATED             : March 27, 2007
INVENTOR(S)       : Nishi et al.

It is certified that error appears in the above-identified patent and that said Letters Patent is hereby corrected as shown below:

In column 2, line 25, replace "5713, 1996)" with --5713, 1986)--.

In column 5, line 22, replace "5713, 1996)" with --5713, 1986)--.

Signed and Sealed this

Twenty-third Day of October, 2007

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 2529
<212> TYPE: DNA
<213> ORGANISM: Stenotrophomonas maltophilia
<220> FEATURE:
<221> NAME/KEY: CDS
<222> LOCATION: (126)...(2036)

<400> SEQUENCE: 1
tctacaacgg cttggcacat gtgccatcag tcctaccccc aaagagcgca gaacgcaaag      60
cctgcacaca cttcacccgc cggggcagga gtacgcttgg gactttcctg cccgaggggt     120 cgtcc atg cat gtg cgt gcc gta gca gtt gcc atc gcc ctg agc ctg tcc    170
      Met His Val Arg Ala Val Ala Val Ala Ile Ala Leu Ser Leu Ser
        1               5                  10                  15 agc acc gtg ctg gcc gcc gac acc ccg ccg atg acc ccg gac atc agc        218
Ser Thr Val Leu Ala Ala Asp Thr Pro Pro Met Thr Pro Asp Ile Ser
                 20                  25                  30 ggc aag cct ttc att gcg ccc gat gtc ggc cgc gac tac gac aag cgc        266
Gly Lys Pro Phe Ile Ala Pro Asp Val Gly Arg Asp Tyr Asp Lys Arg
             35                  40                  45 gtg gtg atg gtg ccg atg cgc gac ggt acc agg ctg tac acg gtg atc        314
Val Val Met Val Pro Met Arg Asp Gly Thr Arg Leu Tyr Thr Val Ile
         50                  55                  60 gtg gtg ccc aag ggc gcg cac aat gcc ccg atc ctg ctg acc cgc acg        362
Val Val Pro Lys Gly Ala His Asn Ala Pro Ile Leu Leu Thr Arg Thr
     65                  70                  75 ccc tac gat gct gcc ggc cgc gcc agc cgc agc gat tcg ccg cgc atg        410
Pro Tyr Asp Ala Ala Gly Arg Ala Ser Arg Ser Asp Ser Pro Arg Met
 80                  85                  90                  95
```

-continued

| | |
|---|---|
| cgc gac ctg ctg ccg cag ggg gat gaa gtc ttc gtc gat ggc ggc tat<br>Arg Asp Leu Leu Pro Gln Gly Asp Glu Val Phe Val Asp Gly Gly Tyr<br>100                               105                       110 | 458 |
| atc cgc gtg ttc cag gac atc cgg ggc aag tac ggt tcg gaa ggc gat<br>Ile Arg Val Phe Gln Asp Ile Arg Gly Lys Tyr Gly Ser Glu Gly Asp<br>115                    120                    125 | 506 |
| tat gtg atg acc cgg ccg ctg cgc ggg ccg ttg aac aac acc aag gtc<br>Tyr Val Met Thr Arg Pro Leu Arg Gly Pro Leu Asn Asn Thr Lys Val<br>130                    135                    140 | 554 |
| gac cac tcc acc gat gca tgg gac acc atc gac tgg ttg gtg aaa cac<br>Asp His Ser Thr Asp Ala Trp Asp Thr Ile Asp Trp Leu Val Lys His<br>145                    150                    155 | 602 |
| gtg ccg gaa agc aac ggc aag gtc ggc atg ctg ggc tcg tcg tac gaa<br>Val Pro Glu Ser Asn Gly Lys Val Gly Met Leu Gly Ser Ser Tyr Glu<br>160                    165                    170                    175 | 650 |
| ggc ttc acc gtg gtg atg gcc ctg acc gac ccg cat ccg gcg ctg aag<br>Gly Phe Thr Val Val Met Ala Leu Thr Asp Pro His Pro Ala Leu Lys<br>                        180                    185                    190 | 698 |
| gtg gcc gcc ccg cag agc ccg atg gtc gat ggc tgg atg ggc gac gac<br>Val Ala Ala Pro Gln Ser Pro Met Val Asp Gly Trp Met Gly Asp Asp<br>195                    200                    205 | 746 |
| tgg ctc aac tac ggg gcc ttc cgc cag gtc aat ttc aac tac ttc gca<br>Trp Leu Asn Tyr Gly Ala Phe Arg Gln Val Asn Phe Asn Tyr Phe Ala<br>          210                    215                    220 | 794 |
| atg cag acc gag aag cgc ggc aag ggc acg ccg ctg ccc agc ctg ggc<br>Met Gln Thr Glu Lys Arg Gly Lys Gly Thr Pro Leu Pro Ser Leu Gly<br>225                    230                    235 | 842 |
| tac gac gac tac agc acc ttc ctg cgc atc ggt tcg gcc ggt gac tac<br>Tyr Asp Asp Tyr Ser Thr Phe Leu Arg Ile Gly Ser Ala Gly Asp Tyr<br>240                    245                    250                    255 | 890 |
| gca cgc ttc acc ggc gtg gac cag ctg acc tgg tgg aag aag ctg gtg<br>Ala Arg Phe Thr Gly Val Asp Gln Leu Thr Trp Trp Lys Lys Leu Val<br>                        260                    265                    270 | 938 |
| cag cac ccg gcc tac gat ggc ttc tgg cag ggc cag gcg ctg gat gcg<br>Gln His Pro Ala Tyr Asp Gly Phe Trp Gln Gly Gln Ala Leu Asp Ala<br>275                    280                    285 | 986 |
| gtg atg gcg aag acc ccg ctg aag gtg ccg acc atg tgg ctg cag ggc<br>Val Met Ala Lys Thr Pro Leu Lys Val Pro Thr Met Trp Leu Gln Gly<br>          290                    295                    300 | 1034 |
| ctg tgg gac cag gaa gac atg tgg ggc gcc aac cat gcc tac cag gcg<br>Leu Trp Asp Gln Glu Asp Met Trp Gly Ala Asn His Ala Tyr Gln Ala<br>305                    310                    315 | 1082 |
| atg gaa ggc cgc gac acc ggc aat acc cac aat tac ctg gtg atg ggc<br>Met Glu Gly Arg Asp Thr Gly Asn Thr His Asn Tyr Leu Val Met Gly<br>320                    325                    330                    335 | 1130 |
| ccg tgg cgg cac agc cag gtg aac tac acc ggc aac gag ctg ggt gcg<br>Pro Trp Arg His Ser Gln Val Asn Tyr Thr Gly Asn Glu Leu Gly Ala<br>                        340                    345                    350 | 1178 |
| ctg aag ttc gag ggc gat acc gcg ctg cag ttc cgc cgc gat gtg ctc<br>Leu Lys Phe Glu Gly Asp Thr Ala Leu Gln Phe Arg Arg Asp Val Leu<br>355                    360                    365 | 1226 |
| aag ccg ttc ttc gac cag tac ctg gtg gat ggc gca ccg aag gcc gac<br>Lys Pro Phe Phe Asp Gln Tyr Leu Val Asp Gly Ala Pro Lys Ala Asp<br>370                    375                    380 | 1274 |
| acg ccg ccg gtc ctc atc tac aac acc ggc gaa aac cac tgg gat cgc<br>Thr Pro Pro Val Leu Ile Tyr Asn Thr Gly Glu Asn His Trp Asp Arg<br>385                    390                    395 | 1322 |
| ctg cag ggc tgg ccg cgc agt tgc gac aag ggc tgc acg gcg gcc agc<br>Leu Gln Gly Trp Pro Arg Ser Cys Asp Lys Gly Cys Thr Ala Ala Ser<br>400                    405                    410                    415 | 1370 |

-continued

| | | | | | | | | | | | | | | | | |
|---|---|---|---|---|---|---|---|---|---|---|---|---|---|---|---|---|
| aag | ccg | ctg | tac | ctg | cgt | gcc | ggt | ggc | aag | ctg | gcc | ttc | cag | gca | ccg | 1418 |
| Lys | Pro | Leu | Tyr | Leu | Arg | Ala | Gly | Gly | Lys | Leu | Ala | Phe | Gln | Ala | Pro | |
| | | | 420 | | | | | 425 | | | | | 430 | | | |

| gcg | gcg | ggt | gaa | ggt | gat | ttc | gag | gaa | tac | gtg | tcc | gac | ccg | gcc | aag | 1466 |
| Ala | Ala | Gly | Glu | Gly | Asp | Phe | Glu | Glu | Tyr | Val | Ser | Asp | Pro | Ala | Lys | |
| | | 435 | | | | | 440 | | | | | 445 | | | | |

| ccg | gtg | ccg | ttc | gtg | ccg | cgc | ccg | gtg | cgt | ttt | ggc | gac | cgt | gac | atg | 1514 |
| Pro | Val | Pro | Phe | Val | Pro | Arg | Pro | Val | Arg | Phe | Gly | Asp | Arg | Asp | Met | |
| | 450 | | | | | 455 | | | | | 460 | | | | | |

| tgg | acc | acg | tgg | ctg | gtg | aag | gac | caa | cgt | ttt | gtc | gat | ggt | cgt | ccg | 1562 |
| Trp | Thr | Thr | Trp | Leu | Val | Lys | Asp | Gln | Arg | Phe | Val | Asp | Gly | Arg | Pro | |
| 465 | | | | | 470 | | | | | 475 | | | | | | |

| gat | gtg | ctg | acc | ttc | atc | acc | gaa | ccg | ctg | gcc | gag | ccg | ctg | cgg | atc | 1610 |
| Asp | Val | Leu | Thr | Phe | Ile | Thr | Glu | Pro | Leu | Ala | Glu | Pro | Leu | Arg | Ile | |
| 480 | | | | | 485 | | | | | 490 | | | | | 495 | |

| ggc | ggc | gcg | ccg | gtg | gtg | cat | ctg | cag | gcg | tcc | acc | agt | ggc | acc | gac | 1658 |
| Gly | Gly | Ala | Pro | Val | Val | His | Leu | Gln | Ala | Ser | Thr | Ser | Gly | Thr | Asp | |
| | | | | 500 | | | | | 505 | | | | | 510 | | |

| agc | gac | tgg | gtg | gtg | aag | ctg | atc | gac | gtc | tac | ccg | gat | cag | gaa | gcg | 1706 |
| Ser | Asp | Trp | Val | Val | Lys | Leu | Ile | Asp | Val | Tyr | Pro | Asp | Gln | Glu | Ala | |
| | | | 515 | | | | | 520 | | | | | 525 | | | |

| tca | acg | ccg | gaa | atg | ggt | ggc | tat | gag | ctg | ccg | gtg | tcg | ctg | gcg | atc | 1754 |
| Ser | Thr | Pro | Glu | Met | Gly | Gly | Tyr | Glu | Leu | Pro | Val | Ser | Leu | Ala | Ile | |
| | | 530 | | | | | 535 | | | | | 540 | | | | |

| ttc | cgt | ggg | cgc | tat | cgg | gag | agt | ttc | agc | gac | ccg | aag | ccg | ctg | gca | 1802 |
| Phe | Arg | Gly | Arg | Tyr | Arg | Glu | Ser | Phe | Ser | Asp | Pro | Lys | Pro | Leu | Ala | |
| | 545 | | | | | 550 | | | | | 555 | | | | | |

| gcg | aac | cag | gtg | ctg | ccg | tac | cgc | ttt | gat | ctg | ccc | aat | gcc | aac | cat | 1850 |
| Ala | Asn | Gln | Val | Leu | Pro | Tyr | Arg | Phe | Asp | Leu | Pro | Asn | Ala | Asn | His | |
| 560 | | | | | 565 | | | | | 570 | | | | | 575 | |

| gtg | ttc | cag | aag | ggg | cac | cgg | gtg | atg | gtg | cag | gtg | cag | tcc | agc | ctg | 1898 |
| Val | Phe | Gln | Lys | Gly | His | Arg | Val | Met | Val | Gln | Val | Gln | Ser | Ser | Leu | |
| | | | | 580 | | | | | 585 | | | | | 590 | | |

| ttc | ccg | ctg | tat | gac | cgc | aac | ccg | cag | acc | tac | gtg | ccg | aac | atc | tac | 1946 |
| Phe | Pro | Leu | Tyr | Asp | Arg | Asn | Pro | Gln | Thr | Tyr | Val | Pro | Asn | Ile | Tyr | |
| | | | 595 | | | | | 600 | | | | | 605 | | | |

| ctg | gcc | aag | ccg | ggc | gat | tac | cag | aag | gcc | acg | cag | cgg | gtg | tgg | cac | 1994 |
| Leu | Ala | Lys | Pro | Gly | Asp | Tyr | Gln | Lys | Ala | Thr | Gln | Arg | Val | Trp | His | |
| | | 610 | | | | | 615 | | | | | 620 | | | | |

| agc | gcc | gcg | cag | gcg | agc | tac | gtc | gac | ctg | ccg | gtg | tac | tga | | | 2036 |
| Ser | Ala | Ala | Gln | Ala | Ser | Tyr | Val | Asp | Leu | Pro | Val | Tyr | | | | |
| | 625 | | | | | 630 | | | | | 635 | | | | | |

| | | | | |
|---|---|---|---|---|
| ggcggagaat | ggcgtggtag | tgccggccgc | tggccggcaa | cgcggagcgg | tagcgccggg | 2096 |
| ccatgcccgg | cggatggggt | agtgccggcc | gctggccggc | aacgcggtga | agccggcgcg | 2156 |
| tgtcgaccaa | ggccgacacc | tgccagagca | cgtcagccta | ccttcgaggg | accggtgcgc | 2216 |
| cagcggctgg | gaaccagacc | gaagcgcttg | cggaaggcgg | cggcgaagtt | gctggggtgg | 2276 |
| cggtagccgg | tggcgtccgc | cgcctgttca | acgctccagc | cgtgttcgcg | caggccgcgt | 2336 |
| tcggcgtggt | gcatgcgttg | ttcgtgcagg | tagtcgaaca | ccgagcaccc | gtattgctgc | 2396 |
| acgaagtggc | ggcgcagcga | gctgggactc | atgcaggcca | gctgggccag | ttccaccagg | 2456 |
| ctgtgggcgt | ggctgggatc | gtcgtgcagg | aagccccgca | cgcgttcaat | cgggccaagt | 2516 |
| tggccgcgcc | aaa | | | | | 2529 |

<210> SEQ ID NO 2
<211> LENGTH: 636
<212> TYPE: PRT
<213> ORGANISM: Stenotrophomonas maltophilia

<400> SEQUENCE: 2

```
Met His Val Arg Ala Val Ala Val Ala Ile Ala Leu Ser Leu Ser Ser
 1               5                  10                  15

Thr Val Leu Ala Ala Asp Thr Pro Met Thr Pro Asp Ile Ser Gly
             20                  25                  30

Lys Pro Phe Ile Ala Pro Asp Val Gly Arg Asp Tyr Asp Lys Arg Val
             35                  40                  45

Val Met Val Pro Met Arg Asp Gly Thr Arg Leu Tyr Thr Val Ile Val
 50                  55                  60

Val Pro Lys Gly Ala His Asn Ala Pro Ile Leu Leu Thr Arg Thr Pro
 65                  70                  75                  80

Tyr Asp Ala Ala Gly Arg Ala Ser Arg Ser Asp Ser Pro Arg Met Arg
                 85                  90                  95

Asp Leu Leu Pro Gln Gly Asp Glu Val Phe Val Asp Gly Tyr Ile
                100                 105                 110

Arg Val Phe Gln Asp Ile Arg Gly Lys Tyr Gly Ser Glu Gly Asp Tyr
                115                 120                 125

Val Met Thr Arg Pro Leu Arg Gly Pro Leu Asn Asn Thr Lys Val Asp
130                 135                 140

His Ser Thr Asp Ala Trp Asp Thr Ile Asp Trp Leu Val Lys His Val
145                 150                 155                 160

Pro Glu Ser Asn Gly Lys Val Gly Met Leu Gly Ser Ser Tyr Glu Gly
                165                 170                 175

Phe Thr Val Val Met Ala Leu Thr Asp Pro His Pro Ala Leu Lys Val
                180                 185                 190

Ala Ala Pro Gln Ser Pro Met Val Asp Gly Trp Met Gly Asp Asp Trp
                195                 200                 205

Leu Asn Tyr Gly Ala Phe Arg Gln Val Asn Phe Asn Tyr Phe Ala Met
    210                 215                 220

Gln Thr Glu Lys Arg Gly Lys Gly Thr Pro Leu Pro Ser Leu Gly Tyr
225                 230                 235                 240

Asp Asp Tyr Ser Thr Phe Leu Arg Ile Gly Ser Ala Gly Asp Tyr Ala
                245                 250                 255

Arg Phe Thr Gly Val Asp Gln Leu Thr Trp Lys Lys Leu Val Gln
                260                 265                 270

His Pro Ala Tyr Asp Gly Phe Trp Gln Gly Gln Ala Leu Asp Ala Val
                275                 280                 285

Met Ala Lys Thr Pro Leu Lys Val Pro Thr Met Trp Leu Gln Gly Leu
    290                 295                 300

Trp Asp Gln Glu Asp Met Trp Gly Ala Asn His Ala Tyr Gln Ala Met
305                 310                 315                 320

Glu Gly Arg Asp Thr Gly Asn Thr His Asn Tyr Leu Val Met Gly Pro
                325                 330                 335

Trp Arg His Ser Gln Val Asn Tyr Thr Gly Asn Glu Leu Gly Ala Leu
                340                 345                 350

Lys Phe Glu Gly Asp Thr Ala Leu Gln Phe Arg Arg Asp Val Leu Lys
                355                 360                 365

Pro Phe Phe Asp Gln Tyr Leu Val Asp Gly Ala Pro Lys Ala Asp Thr
    370                 375                 380

Pro Pro Val Leu Ile Tyr Asn Thr Gly Glu Asn His Trp Asp Arg Leu
385                 390                 395                 400

Gln Gly Trp Pro Arg Ser Cys Asp Lys Gly Cys Thr Ala Ala Ser Lys
                405                 410                 415
```

```
Pro Leu Tyr Leu Arg Ala Gly Gly Lys Leu Ala Phe Gln Ala Pro Ala
            420                 425                 430

Ala Gly Glu Gly Asp Phe Glu Glu Tyr Val Ser Asp Pro Ala Lys Pro
        435                 440                 445

Val Pro Phe Val Pro Arg Pro Val Arg Phe Gly Asp Arg Asp Met Trp
    450                 455                 460

Thr Thr Trp Leu Val Lys Asp Gln Arg Phe Val Asp Gly Arg Pro Asp
465                 470                 475                 480

Val Leu Thr Phe Ile Thr Glu Pro Leu Ala Glu Pro Leu Arg Ile Gly
                485                 490                 495

Gly Ala Pro Val Val His Leu Gln Ala Ser Thr Ser Gly Thr Asp Ser
            500                 505                 510

Asp Trp Val Val Lys Leu Ile Asp Val Tyr Pro Asp Gln Glu Ala Ser
        515                 520                 525

Thr Pro Glu Met Gly Gly Tyr Glu Leu Pro Val Ser Leu Ala Ile Phe
    530                 535                 540

Arg Gly Arg Tyr Arg Glu Ser Phe Ser Asp Pro Lys Pro Leu Ala Ala
545                 550                 555                 560

Asn Gln Val Leu Pro Tyr Arg Phe Asp Leu Pro Asn Ala Asn His Val
                565                 570                 575

Phe Gln Lys Gly His Arg Val Met Val Gln Val Gln Ser Ser Leu Phe
            580                 585                 590

Pro Leu Tyr Asp Arg Asn Pro Gln Thr Tyr Val Pro Asn Ile Tyr Leu
        595                 600                 605

Ala Lys Pro Gly Asp Tyr Gln Lys Ala Thr Gln Arg Val Trp His Ser
610                 615                 620

Ala Ala Gln Ala Ser Tyr Val Asp Leu Pro Val Tyr
625                 630                 635

<210> SEQ ID NO 3
<211> LENGTH: 25
<212> TYPE: PRT
<213> ORGANISM: Stenotrophomonas maltophilia
<220> FEATURE:
<221> NAME/KEY: PEPTIDE
<222> LOCATION: (1)...(25)

<400> SEQUENCE: 3

Val Pro Thr Met Trp Leu Gln Gly Leu Trp Asp Gln Glu Asp Met Trp
  1               5                  10                  15

Gly Ala Asn His Ala Tyr Gln Ala Met
                20                  25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: K1 primer

<400> SEQUENCE: 4
tgggaycarg argayatgtg ggg                                           23

<210> SEQ ID NO 5
<211> LENGTH: 8
<212> TYPE: PRT
<213> ORGANISM: Stenotrophomonas maltophilia
<220> FEATURE:
<221> NAME/KEY: PEPTIDE
<222> LOCATION: (1)...(8)
```

```
<400> SEQUENCE: 5

Trp Asp Gln Glu Asp Met Trp Gly
 1               5

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: K-Nde I-4
      primer

<400> SEQUENCE: 6
ggaattccat atgcatgtgc gtgccgtagc                                          30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: K-BamH I-1
      primer

<400> SEQUENCE: 7
cgcggatcct cagtacaccg gcaggtc                                             27

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: MT-197
      primer

<400> SEQUENCE: 8
aaaaagcagg ctggcacgac aggtttcccg actgga                                   36

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: MT-198
      primer

<400> SEQUENCE: 9
agaaagctgg gtggatcctc agtacaccgg caggtcga                                 38

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: attB1
      primer

<400> SEQUENCE: 10
ggggacaagt ttgtacaaaa aagcaggct                                           29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: attB2
      primer
```

```
<400> SEQUENCE: 11
ggggaccact ttgtacaaga aagctgggt                                              29

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: MT-216
      primer

<400> SEQUENCE: 12
cgcctctaga agcgattcgc cgcgcatgcg cgacc                                       35

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: MT-219
      primer

<400> SEQUENCE: 13
gcacaagctt cttccaccag gtcagctgg                                              29

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: MT-217
      primer

<400> SEQUENCE: 14
tcgcttctag aggcgcggcc ggcagcatcg tagggc                                      36

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: MT-218
      primer

<400> SEQUENCE: 15
ggaagaagct tgtgcagcac ccggcc                                                 26
```